US010988795B2

(12) United States Patent
Turchinovich et al.

(10) Patent No.: US 10,988,795 B2
(45) Date of Patent: Apr. 27, 2021

(54) SYNTHESIS OF DOUBLE-STRANDED NUCLEIC ACIDS

(71) Applicants: RUPRECHT-KARLS-UNIVERSITAT HEIDELBERG, Heidelberg (DE); DEUTSCHES KREBSFORSCHUNGSZENTRUM STIFTUNG DES OFFENTLICHEN RECHTS, Heidelberg (DE)

(72) Inventors: Andrey Turchinovich, Mannheim (DE); Harald Surowy, Heidelberg (DE); Barbara Burwinkel, Heidelberg (DE)

(73) Assignees: RUPRECHT-KARLS-UNIVERSITAT HEIDELBERG; DEUTSCHES KREBSFORSCH ( * ) Notice: Subject to any disclaimer, the term of this patent is extended or adjusted under 35 U.S.C. 154(b) by 713 days.

(21) Appl. No.: 15/309,237

(22) PCT Filed: May 15, 2015

(86) PCT No.: PCT/EP2015/060777
§ 371 (c)(1),
(2) Date: Nov. 7, 2016

(87) PCT Pub. No.: WO2015/173402
PCT Pub. Date: Nov. 19, 2015

(65) Prior Publication Data
US 2019/0032110 A1 Jan. 31, 2019

(30) Foreign Application Priority Data
May 14, 2014 (EP) .................................. 14168313

(51) Int. Cl.
C12Q 1/68 (2018.01)
C07H 21/00 (2006.01)
C12Q 1/6806 (2018.01)
C12N 15/10 (2006.01)

(52) U.S. Cl.
CPC ....... C12Q 1/6806 (2013.01); C12N 15/1093 (2013.01); C12N 15/1096 (2013.01); C12Q 2521/107 (2013.01); C12Q 2525/121 (2013.01); C12Q 2525/155 (2013.01); C12Q 2525/161 (2013.01); C12Q 2525/173 (2013.01); C12Q 2525/191 (2013.01); C12Q 2531/113 (2013.01); C12Q 2535/122 (2013.01)

(58) Field of Classification Search
CPC .................................. C12Q 1/68; C07H 21/00
See application file for complete search history.

(56) References Cited

U.S. PATENT DOCUMENTS

| 4,661,450 A * | 4/1987 | Kempe | C12N 15/1096 435/320.1 |
| 5,962,272 A * | 10/1999 | Chenchik | C12Q 1/6855 435/91.1 |
| 2001/0053519 A1* | 12/2001 | Fodor | B82Y 30/00 435/6.11 |
| 2004/0161762 A1* | 8/2004 | Virtanen | C12N 9/1241 435/6.16 |
| 2008/0009420 A1 | 1/2008 | Schroth et al. | |
| 2008/0182239 A1* | 7/2008 | Mullinax | C12Q 1/6811 435/6.14 |
| 2010/0062494 A1* | 3/2010 | Church | C12Q 1/6855 435/91.2 |
| 2012/0115143 A1* | 5/2012 | Livak | C12Q 1/682 435/6.11 |
| 2012/0283145 A1* | 11/2012 | Wang | C12N 15/65 506/26 |
| 2014/0045188 A1 | 2/2014 | Gou et al. | |
| 2014/0066318 A1* | 3/2014 | Frisen | C12Q 1/6816 506/3 |
| 2014/0094383 A1* | 4/2014 | Lee | G01N 33/56983 506/9 |
| 2014/0113332 A1 | 4/2014 | Betts et al. | |
| 2014/0242581 A1 | 8/2014 | Johnson | |
| 2015/0105277 A1* | 4/2015 | Stewart | C12Q 1/6883 506/9 |
| 2015/0344942 A1* | 12/2015 | Frisen | C12Q 1/6841 506/2 |
| 2019/0264268 A1* | 8/2019 | Frisen | C12Q 1/6837 |

FOREIGN PATENT DOCUMENTS

| CN | 1 330 718 A | 10/1990 |
| CN | 101 948 811 | 1/2011 |
| CN | 102676677 | 9/2012 |
| WO | WO 00/20612 | 4/2000 |
| WO | WO 02/06319 | 1/2001 |
| WO | WO 2013/011378 A1 | 1/2013 |
| WO | 2013/123442 A1 | 8/2013 |
| WO | 2015/057319 A1 | 4/2015 |
| WO | WO 2018/035364 * | 2/2018 |

OTHER PUBLICATIONS

Zhu et al. Biotechniques 30(4) : 892 (Year: 2001).*
Burkard et al., Poly (A) Polymerase and Poly(G) Polymerase in Wheat Chloroplasts. PNAS 71 (2) : 389 (Year: 1974).*
Motea et al.,Ternninal Deoxynucleotidyl Transferase: The Story of a Misguided DNA Polymerase. Biochim Biophys Acta 1804(5): 1151 (Year: 2010).*

(Continued)

Primary Examiner — Ethan C Whisenant
(74) Attorney, Agent, or Firm — McDonnell Boehnen Hulbert & Berghoff LLP

(57) ABSTRACT

The present invention relates to a method for the synthesis of double-stranded nucleic acids from a wide variety of samples and comprises the use of these nucleic acids for deep sequence analysis. Also, the present invention relates to specific reagents used in the method of the present invention. Further, the invention relates to kits comprising reagents for the method of the invention and use of said kits.

20 Claims, 9 Drawing Sheets

Figure 1:
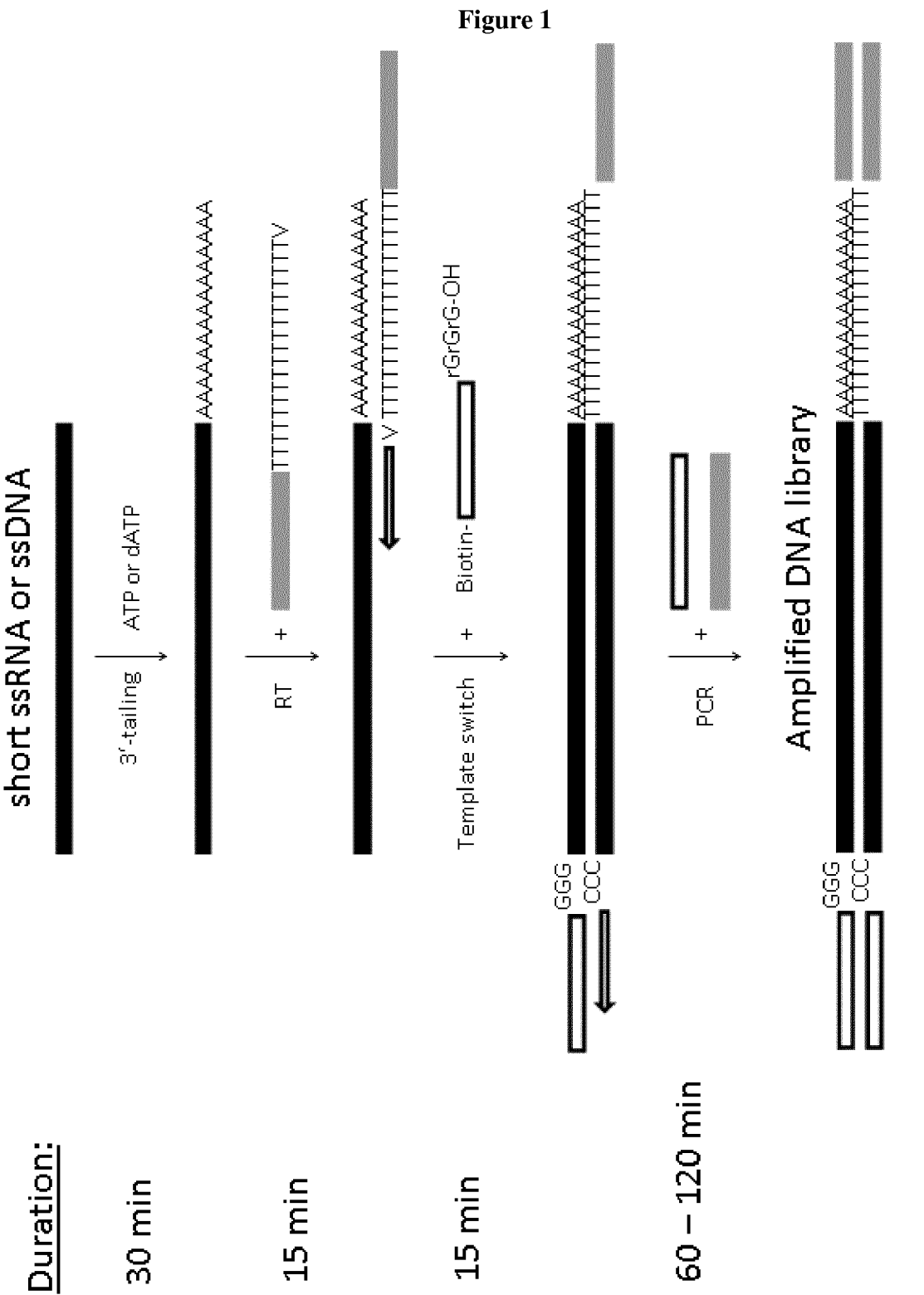

Specification includes a Sequence Listing.

(56) References Cited

OTHER PUBLICATIONS

Tjaden et al., Target prediction for small, noncoding RNAs in bacteria. Nucleic Acids Research 34 (9) : 2791 (Year: 2006).*
Zhu et al.*
Burkard et al., Poly (A) polymerase and Poly(G) polymerase in Wheat Chloroplastr. PNAS 71(2) : 389 (Year: 1974).*
Haff et al., The Polyadenylate Polymerase from Yeast. J. of Biological Che,mistry 250(5): 1838 (Year: 1975).*
Saiki et al., Nature 324 : 163 (Year: 1986).*
Petalidis et al.,Nucleic Acids Research 31(22) : e142. (Year: 2003).*
Lucigen Poly(A) Polymerase Tailing Kit. (Year: 2005).*
Miler et al., Sequencing the nuclear genome of the extinct woolly mammoth. Nature 456 :387 (Year: 2008).*
Maxon et al.,Deep sequencing of tomato short RNAs identifies microRNAs targeting genes involved in fruit ripening. Genome Research 18: 1602 (Year: 2008).*
Buermans et al., New methods for next generation sequencing based micro RNA expression profiling. BMC Genomics 1:716 (Year: 2010).*
Zhao et al., A Simple and Fast Method for Profiling MicroRNA Expression from Low-input Total RNA by Microarray . Life 64(7) : 612 (Year: 2012).*
Zhao et al., A Simple and Fast Method for Profiling MicroRNA Expression from Low-input Total RNA by Microarray. IUBMB Life 64(7) : 612-616 (Year: 2012).*
Zhu et al., Reverse Transcriptase Template switching : A Smart Approach for Full-Length cDNA Library Construction. Biotechniques 30(4) : 892-897 (Year: 2001).*
European Examination Report for 15724585.3, dated Mar. 25, 2019.
Botero, et al., "Poly(A) Polymerase Modification and Reverse Transcriptase PCR Amplification of Environmental RNA", Applied and Environmental Microbiology, vol. 71, No. 3, Mar. 1, 2005 (Mar. 1, 2005 ), pp. 1267-1275.
Preliminary Report on Patentability for PCT/EP2015/060777, dated Nov. 15, 2016.
Hoshino Tatsuhiko et al: "A comparative study of microbial diversity and community structure in marine sediments using poly(A) tailing and reverse transcription-FOR", Jun. 2013, Frontiers in Microbiology, 4 (160).
The International Search Report (ISR) for PCT/EP2015/060777, dated Jul. 13, 2015, pp. 1-5.
The Written Opinion of the International Searching Authority for PCT/EP2015/060777, dated Jul. 13, 2015, pp. 1-5.
Hoshino, Tatsuhiko et al., "A comparative study of microbial diversity and community structure in marine sediments using poly(A) tailing and reverse transcription-PCR" Frontiers in Microbiology (2013), vol. 4, Article 160, pp. 1-8.
Shi, Rui et al., "Poly(T) Adaptor RT-PCR" Methods in Molecular Biology (2012), vol. 822, pp. 53-66.
Picelli, Simone et al., "Full-length RNA-seq from single cells using Smart-seq2" Nature Protocols (2014), vol. 9(1), pp. 171-181.
Turchinovich, Andrey et al., "Capture and amplification by tailing and switching (CATS)" RNA Biology (2014), vol. 11(7), pp. 817-828.
Zhang et al., "Analyses of miRNA species and their relative abundance in IGROV-1/CP cells using Illumina sequence technology," Journal of Instrumental Analysis 28(2):129-134 (Feb. 2009). English abstract included. Abstract Only.
English translation of Search Report from Chinese Patent Application No. 201580024928.6; dated Nov. 7, 2019, pp. 1-3.
Guo et al., Genetic Engineering Pharmacy, Second Military Medical University Press; Oct. 31, 2000, p. 34. English summary provided in IDS transmittal letter.
English translation of Search Report from Chinese Patent Application No. 201580024928.6; dated Jul. 11, 2020, pp. 1-2.
Zhang et al., "Time-resolved probes based on guanine/thymine-rich DNA-sensitized luminescence of terbium (III)" Analytical Chemistry 85:11665-674 (2013).

* cited by examiner

Figure 2A

Figure 2B
cel-miR-39 (synthetic 22 nt RNA): ucaccggguguaaaucagcuug
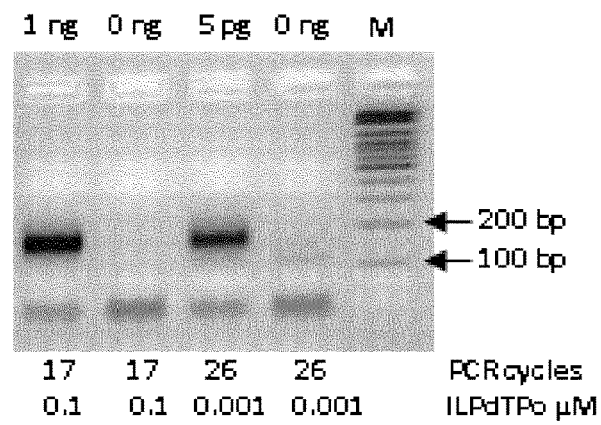
cel-miR-39 (synthetic 22 nt DNA): tcaccgggtgtaaatcagcttg
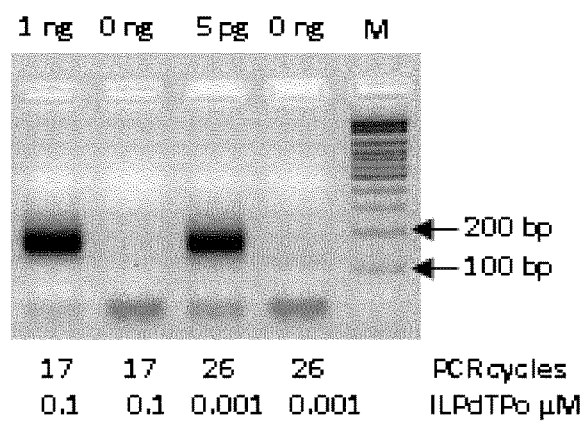

Figure 4

A

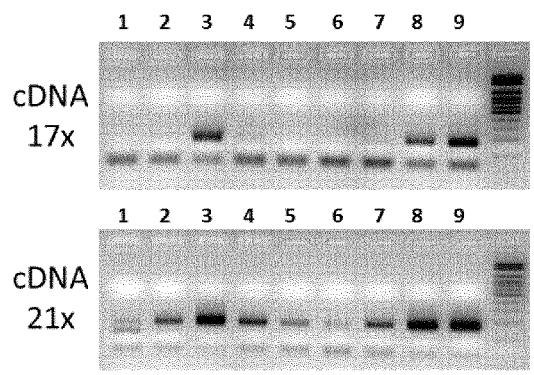

Template Switch Oligo (TSO)

1 – GTTCAGAGTTCTACAGTCCGACGATCGGG
2 – rGrTrTrCrArGrArGrTrTrCrTrArCrArGrTrCrCrGrArCrGrArTrCrGrGrG
3 – GTTCAGAGTTCTACAGTCCGACGATCrGrGrG
4 – GTTCAGAGTTCTACAGTCCGACGATCrGrGrGrG
5 – GTTCAGAGTTCTACAGTCCGACGATCrGrGrG-Phosphate
6 – GTTCAGAGTTCTACAGTCCGACGATCrGrGrG-Biotin
7 – Biotin-GTTCAGAGTTCTACAGTCCGACGATCrGrGrG-ddC
8 – Biotin-GTTCAGAGTTCTACAGTCCGACGATCrGrGrG
9 – GAbAbAbGTTCAGAGTTCTACAGTCCGACGATCrGrGrG

B

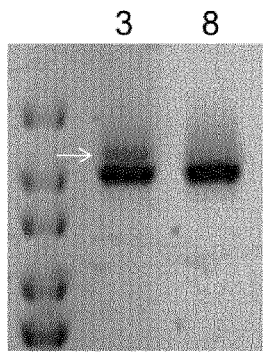

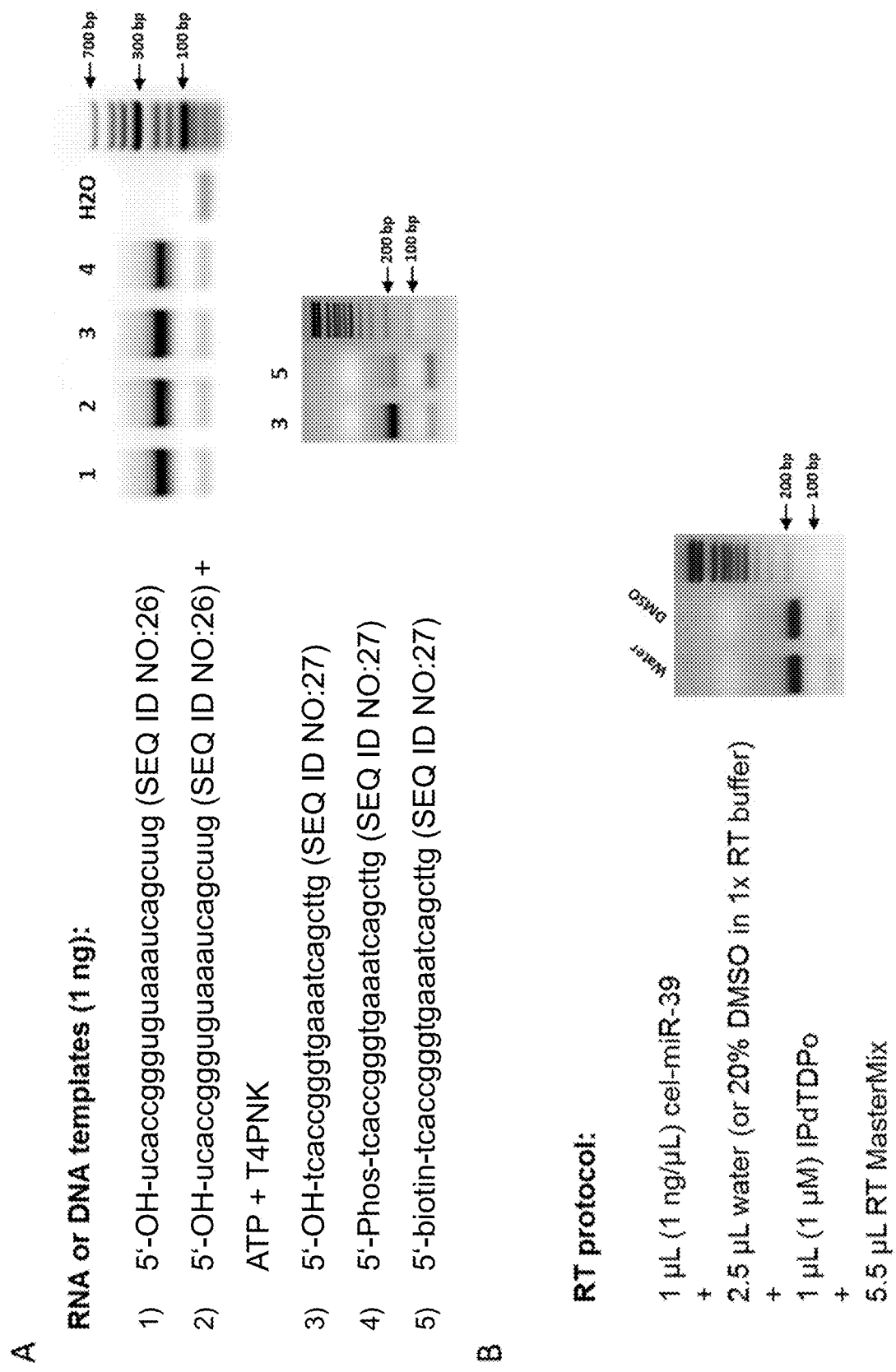

Figure 6
A  Poly(A) enriched RNA from U2OS cells
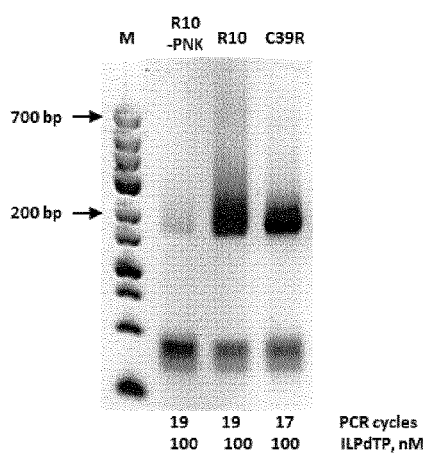
B  Bisulfite-converted DNA from U2OS cells
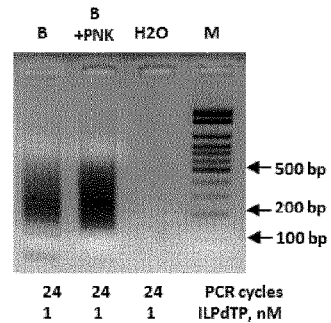
C  Circulating blood plasma DNA
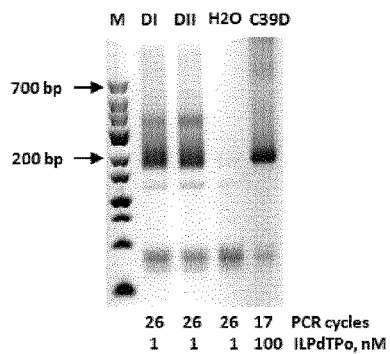
D  Circulating blood plasma RNA
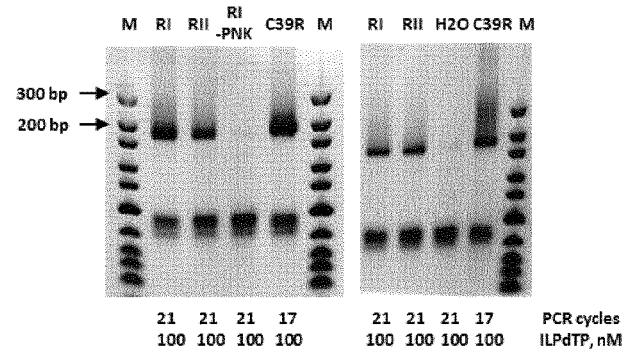

30A: AGACGTGTGCTCTTCCGATCTTTTTTTTTTTTTTTTTTTTTTTTTTTTTV

15A: AGACGTGTGCTCTTCCGATCTTTTTTTTTTTTTTTV

20G: AGACGTGTGCTCTTCCGATCTTTTTTTTTTGTTTTTTTTTTV

16G: AGACGTGTGCTCTTCCGATCTTTTTTTTTGTTTTTTTV

Figure 8
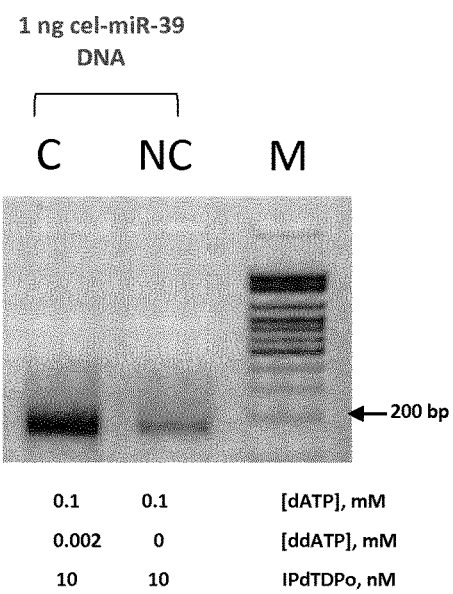
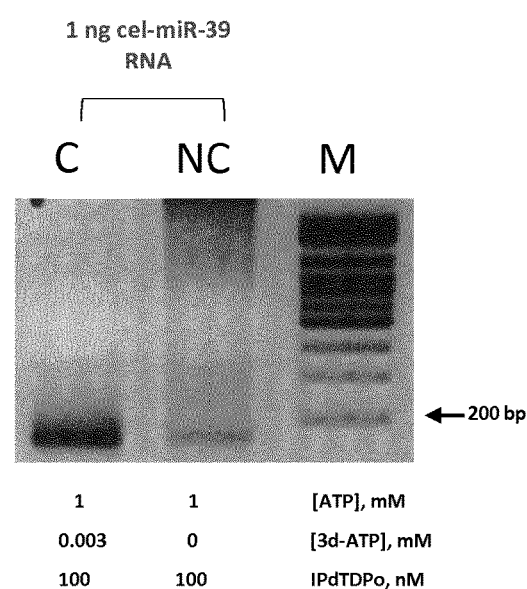

SEQUENCE LISTING

```
<160> NUMBER OF SEQ ID NOS: 31

<210> SEQ ID NO 1
<211> LENGTH: 20
<212> TYPE: DNA
<213> ORGANISM: Artificial Sequence
<220> FEATURE:
<223> OTHER INFORMATION: synthetic

<400> SEQUENCE: 1
aatgatacgg cgaccaccga                                              20

<210> SEQ ID NO 2
<211> LENGTH: 20
<212> TYPE: DNA
<213> ORGANISM: Artificial Sequence
<220> FEATURE:
<223> OTHER INFORMATION: synthetic

<400> SEQUENCE: 2
ttactatgcc gctggtggct                                              20

<210> SEQ ID NO 3
<211> LENGTH: 21
<212> TYPE: DNA
<213> ORGANISM: Artificial Sequence
<220> FEATURE:
<223> OTHER INFORMATION: synthetic
```

```
<400> SEQUENCE: 3
caagcagaag acggcatacg a                                              21

<210> SEQ ID NO 4
<211> LENGTH: 21
<212> TYPE: DNA
<213> ORGANISM: Artificial Sequence
<220> FEATURE:
<223> OTHER INFORMATION: synthetic

<400> SEQUENCE: 4
gttcgtcttc tgccgtatgc t                                              21

<210> SEQ ID NO 5
<211> LENGTH: 23
<212> TYPE: DNA
<213> ORGANISM: Artificial Sequence
<220> FEATURE:
<223> OTHER INFORMATION: synthetic

<400> SEQUENCE: 5
cctctctatg ggcagtcggt gat                                            23

<210> SEQ ID NO 6
<211> LENGTH: 23
<212> TYPE: DNA
<213> ORGANISM: Artificial Sequence
<220> FEATURE:
<223> OTHER INFORMATION: synthetic

<400> SEQUENCE: 6
ggagagatac ccgtcagcca cta                                            23

<210> SEQ ID NO 7
<211> LENGTH: 30
<212> TYPE: DNA
<213> ORGANISM: Artificial Sequence
<220> FEATURE:
<223> OTHER INFORMATION: synthetic

<400> SEQUENCE: 7
ccatctcatc cctgcgtgtc tccgactcag                                     30

<210> SEQ ID NO 8
<211> LENGTH: 30
<212> TYPE: DNA
<213> ORGANISM: Artificial Sequence
<220> FEATURE:
<223> OTHER INFORMATION: synthetic

<400> SEQUENCE: 8
ggtagagtag ggacgcacag aggctgagtc                                     30

<210> SEQ ID NO 9
<211> LENGTH: 21
<212> TYPE: DNA
<213> ORGANISM: Artificial Sequence
<220> FEATURE:
<223> OTHER INFORMATION: synthetic

<400> SEQUENCE: 9
cgtatcgcct ccctcgcgcc a                                              21
```

```
<210> SEQ ID NO 10
<211> LENGTH: 21
<212> TYPE: DNA
<213> ORGANISM: Artificial Sequence
<220> FEATURE:
<223> OTHER INFORMATION: synthetic

<400> SEQUENCE: 10
gcatagcgga gggagcgcgg t                                              21

<210> SEQ ID NO 11
<211> LENGTH: 21
<212> TYPE: DNA
<213> ORGANISM: Artificial Sequence
<220> FEATURE:
<223> OTHER INFORMATION: synthetic

<400> SEQUENCE: 11
ctatgcgcct tgccagcccg c                                              21

<210> SEQ ID NO 12
<211> LENGTH: 21
<212> TYPE: DNA
<213> ORGANISM: Artificial Sequence
<220> FEATURE:
<223> OTHER INFORMATION: synthetic

<400> SEQUENCE: 12
gatacgcgga acggtcgggc g                                              21

<210> SEQ ID NO 13
<211> LENGTH: 40
<212> TYPE: DNA
<213> ORGANISM: Artificial Sequence
<220> FEATURE:
<223> OTHER INFORMATION: synthetic

<400> SEQUENCE: 13
ccactacgcc tccgctttcc tctctatggg cagtcggtga                          40

<210> SEQ ID NO 14
<211> LENGTH: 41
<212> TYPE: DNA
<213> ORGANISM: Artificial Sequence
<220> FEATURE:
<223> OTHER INFORMATION: synthetic

<400> SEQUENCE: 14
ggtgatgcgg aggcggaaag gagagatacc cgtcagccac t                        41

<210> SEQ ID NO 15
<211> LENGTH: 23
<212> TYPE: DNA
<213> ORGANISM: Artificial Sequence
<220> FEATURE:
<223> OTHER INFORMATION: synthetic

<400> SEQUENCE: 15
ctgccccggg ttcctcattc tct                                            23

<210> SEQ ID NO 16
<211> LENGTH: 23
<212> TYPE: DNA
<213> ORGANISM: Artificial Sequence
<220> FEATURE:
<223> OTHER INFORMATION: synthetic
```

<400> SEQUENCE: 16
gacggggccc aaggagtaag aga                                          23

<210> SEQ ID NO 17
<211> LENGTH: 51
<212> TYPE: DNA
<213> ORGANISM: Artificial Sequence
<220> FEATURE:
<223> OTHER INFORMATION: synthetic

<400> SEQUENCE: 17
agacgtgtgc tcttccgatc tttttttttt tttttttttt tttttttttt t           51

<210> SEQ ID NO 18
<211> LENGTH: 36
<212> TYPE: DNA
<213> ORGANISM: Artificial Sequence
<220> FEATURE:
<223> OTHER INFORMATION: synthetic

<400> SEQUENCE: 18
agacgtgtgc tcttccgatc tttttttttt tttttt                            36

<210> SEQ ID NO 19
<211> LENGTH: 42
<212> TYPE: DNA
<213> ORGANISM: Artificial Sequence
<220> FEATURE:
<223> OTHER INFORMATION: synthetic

<400> SEQUENCE: 19
agacgtgtgc tcttccgatc tttttttttt tgttttttttt tt                    42

<210> SEQ ID NO 20
<211> LENGTH: 38
<212> TYPE: DNA
<213> ORGANISM: Artificial Sequence
<220> FEATURE:
<223> OTHER INFORMATION: synthetic

<400> SEQUENCE: 20
agacgtgtgc tcttccgatc ttttttttttg tttttttt                         38

<210> SEQ ID NO 21
<211> LENGTH: 22
<212> TYPE: RNA
<213> ORGANISM: Artificial Sequence
<220> FEATURE:
<223> OTHER INFORMATION: synthetic

<400> SEQUENCE: 21 ucaccggguug uaaaucagcu ug                                          22

<210> SEQ ID NO 22
<211> LENGTH: 22
<212> TYPE: DNA
<213> ORGANISM: Artificial Sequence
<220> FEATURE:
<223> OTHER INFORMATION: synthetic

<400> SEQUENCE: 22
tcaccgggtg taaatcagct tg                                           22

-continued

<210> SEQ ID NO 23
<211> LENGTH: 29
<212> TYPE: DNA
<213> ORGANISM: Artificial Sequence
<220> FEATURE:
<223> OTHER INFORMATION: synthetic

<400> SEQUENCE: 23
gttcagagtt ctacagtccg acgatcggg                                              29

<210> SEQ ID NO 24
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_RNA
<222> LOCATION: (1)..(29)
<223> OTHER INFORMATION: ribose backbone

<400> SEQUENCE: 24
gttcagagtt ctacagtccg acgatcggg                                              29

<210> SEQ ID NO 25
<211> LENGTH: 26
<212> TYPE: DNA
<213> ORGANISM: Artificial Sequence
<220> FEATURE:
<223> OTHER INFORMATION: synthetic

<400> SEQUENCE: 25
gttcagagtt ctacagtccg acgatc                                                 26

<210> SEQ ID NO 26
<211> LENGTH: 22
<212> TYPE: RNA
<213> ORGANISM: Artificial Sequence
<220> FEATURE:
<223> OTHER INFORMATION: synthetic

<400> SEQUENCE: 26
ucaccgggug uaaaucagcu ug                                                     22

<210> SEQ ID NO 27
<211> LENGTH: 21
<212> TYPE: DNA
<213> ORGANISM: Artificial Sequence
<220> FEATURE:
<223> OTHER INFORMATION: synthetic

<400> SEQUENCE: 27
tcaccgggtg aaatcagctt g                                                      21

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
aatgatacgg cgaccaccga g                                                      21

```
<210> SEQ ID NO 29
<211> LENGTH: 50
<212> TYPE: DNA
<213> ORGANISM: Artificial Sequence
<220> FEATURE:
<223> OTHER INFORMATION: Synthetic

<400> SEQUENCE: 29
aatgatacgg cgaccaccga gatctacacg ttcagagttc tacagtccga          50

<210> SEQ ID NO 30
<211> LENGTH: 169
<212> TYPE: DNA
<213> ORGANISM: Artificial Sequence
<220> FEATURE:
<223> OTHER INFORMATION: Synthetic

<400> SEQUENCE: 30
aatgatacgg cgaccaccga gatctacacg ttcagagttc tacagtccga cgatcgggtc   60
accgggtgta aatcagcttg aaaaaaaaaa aaaaaaaaaa aaaaaaaaaa agatcggaag  120
agcacacgtc tgaactccag tcacatcacg atctcgtatg cctgtcttc             169

<210> SEQ ID NO 31
<211> LENGTH: 58
<212> TYPE: DNA
<213> ORGANISM: Artificial Sequence
<220> FEATURE:
<223> OTHER INFORMATION: Synthetic

<400> SEQUENCE: 31
gaagacggca tacgagatcg tgatgtgact ggagttcaga cgtgtgctct tccgatct    58
```

SYNTHESIS OF DOUBLE-STRANDED NUCLEIC ACIDS

CROSS-REFERENCE TO RELATED APPLICATION

This application is a national stage application of International Patent Application No. PCT/EP2015/060777 filed May 15, 2015, which claims priority to European Patent Application No. 14168313.6, filed May 14, 2014, which are both hereby incorporated by reference in their entirety.

The present invention relates to a method for the synthesis of double-stranded nucleic acids from a wide variety of samples and comprises the use of these nucleic acids for deep sequence analysis. Also, the present invention relates to specific reagents used in the method of the present invention. Further, the invention relates to kits comprising reagents for the method of the invention and use of said kits.

BACKGROUND OF THE INVENTION

Massive parallel sequencing (MPS) of nucleic acids requires the preparation of amplified libraries where the region of the DNA to be sequenced is located between known 5'- and 3'-terminal sequences. Current methods for MPS libraries construction utilize either RNA or DNA adaptor ligation to the 5'- and 3'-ends of the RNA or DNA samples. Ligation of adaptors is not only time consuming but also a process of low efficiency that requires microgram inputs of nucleic acid samples. In addition, the resulting cDNA libraries are contaminated with adaptors cross- and self-ligation by-products and require additional purification steps both before and after pre-amplification. More than a decade ago, Clontech Laboratories described a method that harnesses the template switching activity of the Moloney murine leukemia virus reverse transcriptase (MMLV-RT) to attach adaptors of choice to the 5'-end of cDNA generated from of poly(A) tailed mRNA molecules. At the same time, a 3'-adaptor sequence was incorporated into poly(dT) reverse transcription primer. This principle, named SMART, is currently used in an Illumina Ultra Low RNA sequencing kit (Clontech) to generate full length cDNA copies of mRNA molecules from a single cell. However, the method still requires subsequent to the template synthesis (1) fragmentation of amplified cDNA, (2) ligation of platform-specific 5'/3'-end adaptors and (3) pre-amplification of adaptors-ligated DNA fragments. Although the SMART method is capable of preparing cDNA for sequencing from single-cell amounts of RNA, it is time consuming, expensive and restricted to mRNA sequencing. So far, the approach of using template switching activity of MMLV-RT has not been yet applied to sequence (1) RNA molecules other than long RNAs and (2) any DNA molecules. The present invention describes a method to generate ready-to-sequence double or single stranded DNA, preferably DNA libraries from picogram (pg) amounts of either RNA or DNA molecules in a time frame of only a few hours. Small (<150 bp) RNAs or DNAs (e.g. miRNA (microRNAs), piRNAs (piwiRNAs), degraded or bisulfite-converted DNA) can be used as an input directly. However, long RNA or DNA has to be first fragmented by a corresponding approach (e.g. sonication for DNA or $Mg^{2+}$ incubation for RNA). The method of the invention provides several advantages, which include a dramatic reduction in time required to provide ready to sequence DNA, which may be based on DNA or RNA, the method is drastically cheaper than any of the prior art methods. Current commercial kits for cDNA library preparation for next generation sequencing of RNA and DNA are priced between $200 and $500 per samples depending on the application, type of the kit and brand of the supplier. The rough estimates of the costs required for a single DNA library preparation using the method of the invention is at least 20-fold lower, and the method of the invention will permit sequencing of nucleic acids from sources from which sequencing was impossible before due to the minimal amounts of DNA and/or RNA that could be obtained from the sample. Examples of those include: DNA and RNA from small (diagnostic) amounts of liquid and solid biopsies, targeted compartments of the cells (e.g. micronuclei, endoplasmic reticulum), fossils, remnants of the extinct organisms, and forensics samples containing minute and highly fragmented DNA molecules. The present invention is based in part on the discovery that DNA can also serve as a substrate for a reverse transcriptase.

SUMMARY OF THE INVENTION

In a first aspect the present invention provides a method for the synthesis of double stranded nucleic acid with a defined 3' and 5' terminal nucleotide sequence from a sample comprising single stranded nucleic acid comprising the steps of:
a) providing a sample comprising single stranded or double stranded nucleic acid, optionally denaturing the double stranded nucleic acid;
b) adding at least 5, preferably between 10 and 50 consecutive nucleotides to the 3-terminus of the single stranded or double stranded nucleic acid,
c) hybridizing a priming oligonucleotide complementary to the added nucleotide sequence and synthesizing a cDNA or cRNA with a template dependent DNA or RNA polymerase to generate a double stranded nucleic acid,
d) hybridizing a template switching oligonucleotide (TSO) to said double stranded nucleic acid, and
e) extending the 3' end of the cDNA or cRNA strand to synthesize a double stranded nucleic acid, wherein one strand of the nucleic acid comprises the priming oligonucleotide, and a cDNA or a cRNA that is complementary to the single stranded nucleic acid and to the template switching oligonucleotide.

In a second aspect the present invention provides a priming oligonucleotide comprising the following sequence elements:

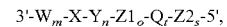

$$3'\text{-}W_m\text{-}X\text{-}Y_n\text{-}Z1_o\text{-}Q_r\text{-}Z2_s\text{-}5',$$

wherein
W at each instance is independently selected from dA, dG, dC, dT and dU;
X is selected from dA, dG, dC, dT, dU, rA, rG, rC, rT and rU;
Y is a polynucleotide of at least 10 nucleotides length, wherein 80% or more of the sequence is composed of an identical nucleotide or dinucleotide selected from dA, dG, dC, dT, dU, rA, rG, rC, rT, rU, AC, AG, AT, AU, CA, CG, CT, CU, GA, GC, GT, GU, TA, TC, TG, TU, AA, CC, GG, TT, UU, UA, UC, UG, and UT, wherein the other at most 20% or less of the sequence is composed of nucleotides or dinucleotides that are different from the major nucleotide or dinucleotide and also selected from dA, dG, dC, dT, dU, rA, rG, rC, rT, rU, AC, AG, AT, AU, CA, CG, CT, CU, GA, GC, GT, GU, TA, TC, TG, TU, AA, CC, GG, TT, UU, UA, UC, UG, and/or UT, with the proviso that X is different from the nucleotide or dinucleotide that constitutes the majority of Y;

Q is a sequence of consecutive degenerate (wobble) DNA bases, preferably selected from N, V, H, D, B and J, wherein N is the product of the incorporation of a nucleotide from an equimolar mixture of dA, dT, dC and dG; B is the product of the incorporation of a nucleotide from an equimolar mixture of dT, dC and dG; D is the product of the incorporation of a nucleotide from an equimolar mixture of dA, dT and dG; H is the product of the incorporation of a nucleotide from an equimolar mixture of dA, dT and dC; V is the product of the incorporation of a nucleotide from an equimolar mixture of dA, dC and dG, J is the product of the incorporation of a nucleotide from a mixture of (0-100% dA) to (0-100% dG) to (0-100% dC) to (0-100% dT) to (0-100% dU) to (0-100% rA) to (0-100% rG) to (0-100% rC) to (0-100% rT) to (0-100% rU);

Z1 is a polynucleotide of at least 5 nucleotides length of defined sequence, wherein the sequence is different from $W_m$-X-$Y_n$, preferably the sequence is also different from $Q_r$-Z2$_s$;

Z2 is a polynucleotide of at least 5 nucleotides length of defined sequence, wherein the sequence is different from Wm-X-$Y_n$-Z1$_o$-$Q_r$;

m is an integer of 0 to 6, i.e. 0, 1, 2, 3, 4, 5 or 6;

n is an integer of 10 to 100, if Y is selected from dA, dG, dC, dT, dU, rA, rG, rC, rT, and rU, an integer of 5 to 50, if Y is selected from AC, AG, AT, AU, CA, CG, CT, CU, GA, GC, GT, GU, TA, TC, TG, TU, AA, CC, GG, TT, UU, UA, UC, UG and UT;

o is 0 or 1;

s is 0 or 1; and t is an integer of 0 to 6, i.e. 0, 1, 2, 3, 4, 5 or 6.

In a third aspect the present invention provides a template switching oligonucleotide comprising the following sequence elements

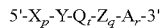

wherein

X is a chemical group selected from the group consisting of amino, biotin, glycerol, cholesterol, digoxigenin, fluoro residue or nucleotide derivatives including abasic nucleotides, dideoxy-ribonucleotides, 3'-deoxynucleotides, 2'-deoxyinosine, 2'-deoxyuridine;

Y is a known oligonucleotide sequence;

Q is a sequence of consecutive degenerate (wobble) DNA bases, preferably selected from N, V, H, D, B and J, wherein N is the product of the incorporation of a nucleotide from an equimolar mixture of dA, dT, dC and dG; B is the product of the incorporation of a nucleotide from an equimolar mixture of dT, dC and dG; D is the product of the incorporation of a nucleotide from an equimolar mixture of dA, dT and dG; H is the product of the incorporation of a nucleotide from an equimolar mixture of dA, dT and dC; V is the product of the incorporation of a nucleotide from an equimolar mixture of dA, dC and dG, J is the product of the incorporation of a nucleotide from a mixture of (0-100% dA) to (0-100% dG) to (0-100% dC) to (0-100% dT) to (0-100% dU) to (0-100% rA) to (0-100% rG) to (0-100% rC) to (0-100% rT) to (0-100% rU);

Z is a ribonucleotide selected from the group consisting of AMP, CMP, GMP, TMP and UMP, A is a chemical group selected from the group consisting of amino, biotin, glycerol, cholesterol, digoxigenin, phosphate, fluoro residue or nucleotide derivatives including abasic nucleotides, dideoxy-ribonucleotides, 3'-deoxynucleotides, 2'-deoxyinosine, 2'-deoxyuridine;

t is an integer of 0 to 6, i.e. 0, 1, 2, 3, 4, 5 or 6;

p is an integer of 0 to 10, i.e. 0, 1, 2, 3, 4, 5, 6, 7, 8, 9 or 10;

q is an integer of at least 1; and r is an integer of 0 to 10, i.e. 0, 1, 2, 3, 4, 5, 6, 7, 8, 9 or 10.

In a fourth aspect the present invention provides a nucleic acid comprising the priming oligonucleotide of the second aspect of the invention.

In a fifth aspect the invention provides a kit comprising
a) a reagent capable of adding nucleotides to the 3-terminus of the single stranded nucleic acid, preferably an enzyme, more preferably a poly(A)-polymerase or terminal transferase (TT), and optionally a blocking nucleotide preferably 3d-NTP, 3-Me-NTP and ddNTP
b) a reverse transcriptase enzyme,
c) the priming oligonucleotide according to the second aspect, and
d) a template switching oligonucleotide according to the third aspect.

In a sixth aspect the present invention provides an array comprising at least one nucleic acid comprising the priming oligonucleotide of the fourth aspect of the present invention.

In a seventh aspect the present invention provides the use of said kit and the use of the synthesized double-stranded nucleic acid in personalized medicine; therapy monitoring; prediction, prognosis, early detection of human or animal disease or forensic science analysis of nucleic acid sequences of viruses, bacteria, animals or plants or cells derived therefrom.

LIST OF FIGURES

In the following, the content of the figures comprised in this specification is described. In this context please also refer to the detailed description of the invention above and/or below.

FIG. 1: Schematic representation of cDNA preparation methods using a combination of polyA(dA) tailing and template switching capacity of MMLV-RT. Briefly, short single stranded RNA or DNA fragments are polyadenylated or polydeoxyadenylated with either poly(A) polymerase or terminal deoxytransferase. Then, a complementary DNA strand synthesis is carried out in the presence of anchored poly(dT) oligonucleotide containing a custom 3'-adaptor sequence. Optionally, the oligonucleotide comprises three different nucleotides at its 3' prime end, i.e. C, G, or A (=V in the schematic representation of FIG. 1). When reverse transcriptase reaches the 5' end of the RNA (or DNA) template, the enzyme's terminal transferase activity adds additional nucleotides (predominantly dC) that are not encoded by the template. On the next step, the template switching oligonucleotide containing three terminal rG nucleotides and custom 5'-adaptor sequences is added to the RT reaction and serves as second template for the reverse transcriptase. The complementary interaction of the three consecutive rG nucleotides at the 3'-end of the TSO and the dC-rich extended sequence of the cDNA are thought to promote template switching. The second cDNA strand is generated during the first cycle of the standard PCR reaction from a forward primer which is either fully or partially complementary to the 3'-terminus of the first cDNA strand. Furthermore, the reverse primer used for the PCR amplification of the cDNA (together with forward primer) is either fully or partially complementary to the 3'-terminus of the second cDNA strand.

Figure 2A:
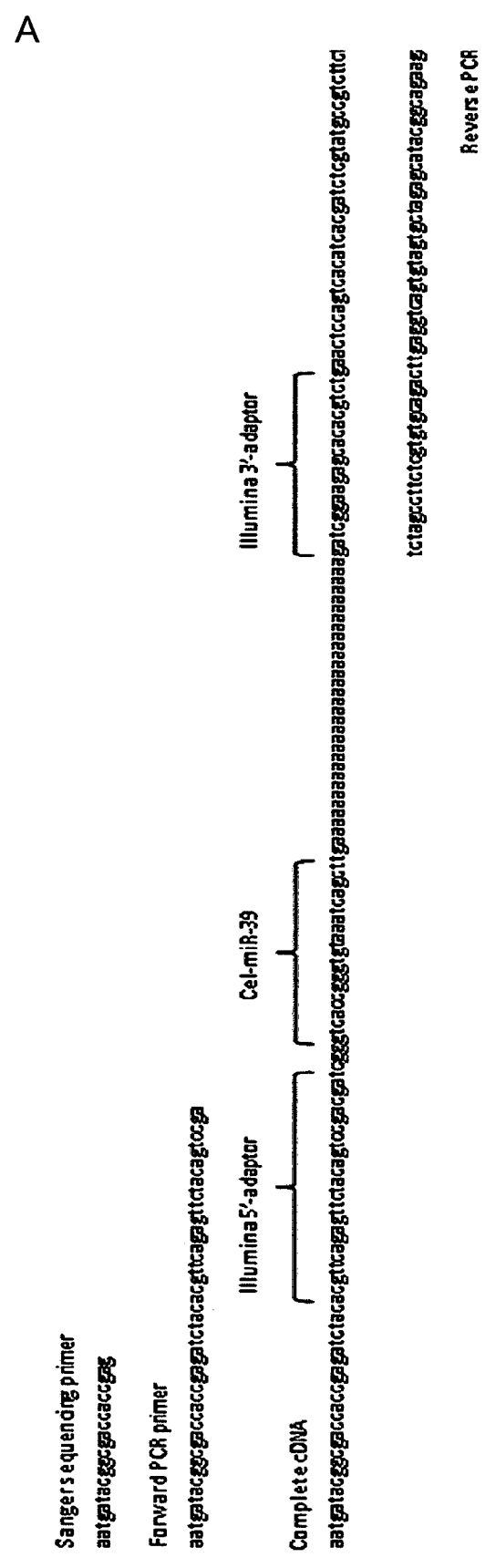

FIG. 2: To construct DNA libraries suitable for Illumina MiSeq or HiSeq platforms we have used adaptor sequences from the NEBnext Small RNA Sequencing Kit (New England Biolabs). The sequence corresponding to the 5'-adaptor was incorporated into the TSO and the 3'-adaptor sequence was used to design a terminal tag of poly(dT) primer (FIG. 2A). Either 1 ng or 5 pg of 22 nt RNA and DNA as inputs for the DNA library preparation were used (FIG. 2B). The efficacy of cDNA synthesis was equal for DNA and RNAs. When using 1 ng of nucleic acids, a single PCR product appeared after 17 PCR pre-amplification cycles (1/100 cDNA to PCR dilution). When 5 pg of nucleic acids were used as an input, the amount of PCR cycles required to pre-amplify cDNA increased to 26. When a 10/100 cDNA to PCR dilution was used, the amount of cycles necessary to generate DNA libraries decreased proportionally (data not shown). The only contaminating by-product in the reaction were the excess of PCR primers, most of which can be removed by column purification. Sanger sequencing has further confirmed that cDNA prepared from synthetic short DNA was pure (data not shown).

Figure 3:
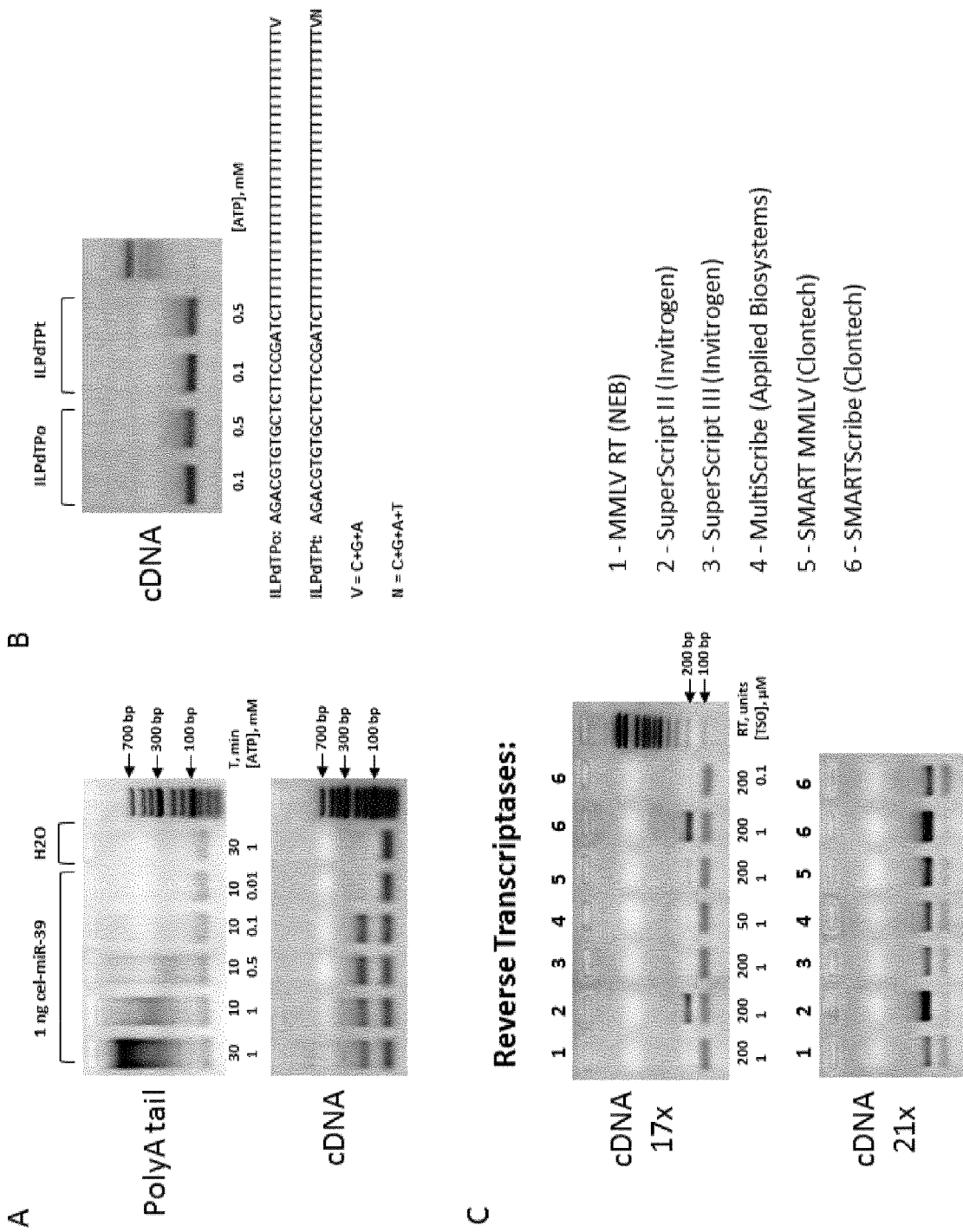

FIG. 3: Critical parameters of the DNA library preparation protocol I. Primarily, the poly(A) tailing reaction is critical for the optimal yield of cDNA. Too long poly(A) tails will eventually decrease the effective concentration of poly(dT) primer, which will not only decrease the amount of cDNA but also lead to a smear of larger by-products on the gel since the poly(dT) primer will hybridize to various sites within the poly(A) tail. FIG. 3A shows in the upper panel an electropherogram obtained after 3% agarose gel electrophoresis of 1 ng cel-miR-39 which was poly(A) tailed using different incubation times and concentrations of ATP. The lower panel shows an electropherogram obtained after 3% agarose gel electrophoresis of DNA libraries generated from 1 ng of corresponding poly(A) tailed cel-miR-39 using 100 nM ILPdTPo. In FIG. 3B an electropherogram obtained after 3% agarose gel electrophoresis of DNA libraries generated from 1 ng of cel-miR-39 (poly(A) tailed for 10 min using different concentrations of ATP) using either 100 nM one-base anchored polydT primer (ILPdTPo) or 100 nM two-base anchored polydT primer (ILPcTPt) is shown. FIG. 3C shows electropherograms obtained after 3% agarose gel electrophoresis of DNA libraries generated from 1 ng of cel-miR-39 (poly(A) tailed for 10 min using 0.1 mM ATP) using MMLV-RT of different brands and using either 1 µM or 0.1 µM of TSO8. Upper figure: PCR amplification of cDNAs was performed for 17 cycles. Lower figure: PCR amplification of cDNAs was performed for 21 cycles. 10 min poly(A)-tailing time and the 0.1 mM of final ATP gave decent results for 22 nt RNA cloning. Secondly, the supplier and the brand of MMLV-RT appeared to be critical for the sensitivity of the approach. Thus, out of 6 commercial MMLV-RTs SuperScribe II (Invitrogen), SMARTScribe RT (Clontech) and SMART RT (Clontech) were most efficient in providing the detectable amounts of cDNA after pre-amplification with the current protocol, while the SuperScribe III (Invitrogen), Multiscribe RT (Applied Biosystems) and M-MLV from NEB required 4 additional cycles of pre-amplification for a DNA library to be visible on agarose gel (FIG. 3C). This phenomenon can be explained by the fact that different MMLV-RT variants might possess different RNAse H and terminal transferase activities (the latter is thought to facilitate the template switching reaction). Thus the selection of an RT with RNAse H activity is preferred.

FIG. 4: Critical parameters for the cDNA library protocol II. An electropherogram obtained after 3% agarose gel electrophoresis of DNA libraries generated from 1 ng cel-miR-39 (poly(A) tailed for 10 min using 0.1 mM ATP) using different template switching oligonucleotides (TSO) at a final concentration of 1 µM is shown. Upper figure: PCR amplification of cDNAs was performed for 17 cycles. Lower figure: PCR amplification of cDNAs was performed for 21 cycles (FIG. 4A). The structure of TSO appears to be critical for the sensitivity and the performance of the method. Both pure DNA and pure RNA TSO failed to yield any adequate amount of the targeted cDNA after 17 cycles of pre-amplification PCR. This could be explained by the fact that a sequence of three riboG has a much stronger affinity for the template switching than three deoxyriboG, while the pure RNA oligonucleotide is prone to forming significant secondary structures that decrease the availability of the 3'-terminus. Furthermore, when TSO with four instead of three terminal riboG nucleotides was used, the yield of the cDNA was dramatically reduced (FIG. 4A), presumably due to the ability of four consecutive G to form quadruplex structures. An option of blocking the terminal 3-OH group of the TSO to prevent its polyA tailing which might occur when poly(A) polymerase is not completely deactivated was also tested. Although thermal deactivation of E. coli poly(A) polymerase for 20 min at 65° C. before the RT reaction was complete, the usage of 3-OH blocked TSO would be mandatory in case that: (1) poly(A) tailing and the RT are performed simultaneously or (2) poly(A) tailing of RNA cannot be heat inactivated. Surprisingly, blocking the 3-OH terminal of TSO with either monophosphate or biotin abrogated the efficacy cDNA synthesis under the conditions used (FIG. 4A). Nevertheless, when 3-OH group of TSO was blocked with phosphate or dideoxycytidine (ddC), similar amounts of cDNA product appeared four PCR cycles later. In FIG. 4B an electropherogram obtained after 4% agarose gel electrophoresis (left) and Agilent Bioanalyser (right) of DNA libraries generated from 1 ng cel-miR-39 (poly(A) tailed for 10 min using 0.1 mM ATP) using 5'-end unblocked TSO3 or 5'-biotin-blocked TSO8 is shown. Note the small fraction of the ~30 bp longer DNA libraries which likely correspond to the products of secondary template switching events (white arrow).

FIG. 5: Critical parameters of the DNA library preparation protocol III. Panel A: Electropherograms obtained after 3% agarose gel electrophoresis of DNA libraries generated from 1 ng of different template cel-miR-39 oligos (RNAs were poly(A) tailed for 10 min using 0.1 mM ATP; DNAs were poly(dA) tailed for 30 min using 0.1 mM ATP) is shown. The efficacy of DNA library synthesis from DNA templates containing 5'-biotin is dramatically lower as compared to the 5'-OH or 5'-Phosphate templates. Panel B: An electropherogram obtained after 3% agarose gel electrophoresis of DNA libraries generated from 1 ng of cel-miR-39 RNA (poly(A) tailed for 10 min using 0.1 mM ATP) using either water or 20% DMSO (5% in final reaction) as a media for RT reaction is shown. The addition of DMSO does not interfere with the efficacy of DNA library preparation.

FIG. 6: DNA libraries preparation from human RNA and DNA. Panel A: An electropherogram obtained after 4% agarose gel electrophoresis (left) of DNA libraries generated from 1 ng of control cel-miR-39 (C39R) and 1 ng of poly(A) enriched RNA isolated from U2OS cells which was fragmented by incubation with magnesium ions for 10 min (R10) was shown. In addition, one DNA library was generated from R10 sample which was not pre-treated with T4 PNK before poly(A) tailing (−RNK labeled). The number of PCR cycles used for the pre-amplification of the cDNA libraries and the concentration of poly(dT) reverse primer (ILPdTPo) are indicated below the electropherogram for each sample. DNA libraries which were sequenced on Illumina MiSeq were cut from the agarose gel, isolated by PureLink Gel Purification kit and analyzed by Agilent Bioanalyser High Sensitivity DNA chips (right). Panel B: Left: An electropherogram obtained after 3% agarose gel electrophoresis of DNA libraries generated from approximately 3 ng of bisulfite-converted DNA from U2OS cells was shwon (FIG. 6B). In addition, one DNA library was generated from B sample which was pre-treated with T4 PNK before poly(dA) reaction (+RNK labeled). In negative control library, 1 µL on water was used (H2O). Right: Agilent Bioanalyser electropherogram showing gel purified DNA libraries generated from 1 ng of poly(A) enriched RNA from U2OS cells which was fragmented by incubation with magnesium ions for 5 min (R5), bisulfite-converted DNA (B) and 1 ng of control cel-miR-39 RNA (C39R). Panel C: Electropherogram obtained after 4% agarose gel electrophoresis (left) and Agilent Bioanalyser (right) of DNA libraries generated from approximately 150 pg of human blood plasma DNA isolated from two healthy donors (DI and DII). In control experiments either water ($H_2O$) or 1 ng of synthetic cel-miR-39 DNA (C39D) were used. The number of PCR cycles used for the pre-amplification of the cDNA libraries and the concentration of poly(dT) reverse primer (ILPdTPo) are indicated below the electropherogram for each sample. Panel D: Electropherogram obtained after 4% agarose gel electrophoresis of DNA libraries generated from approximately 200 pg of human blood plasma RNA isolated from two healthy donors (RI and RII). In control experiments either water ($H_2O$) or 1 ng of synthetic cel-miR-39 RNA (C39R) were used. In addition, DNA libraries were generated from circulating RNA samples which were not pre-treated with T4 PNK before poly(A) tailing (-RNK labeled). The number of PCR cycles used for the pre-amplification of the cDNA libraries and the concentration of poly(dT) reverse primer (ILPdTPo) are indicated below the electropherogram for each sample. DNA libraries from circulating plasma RNA of both individuals were purified from agarose gel, however, only RI library was sequences on Illumina MiSeq.

Figure 7:
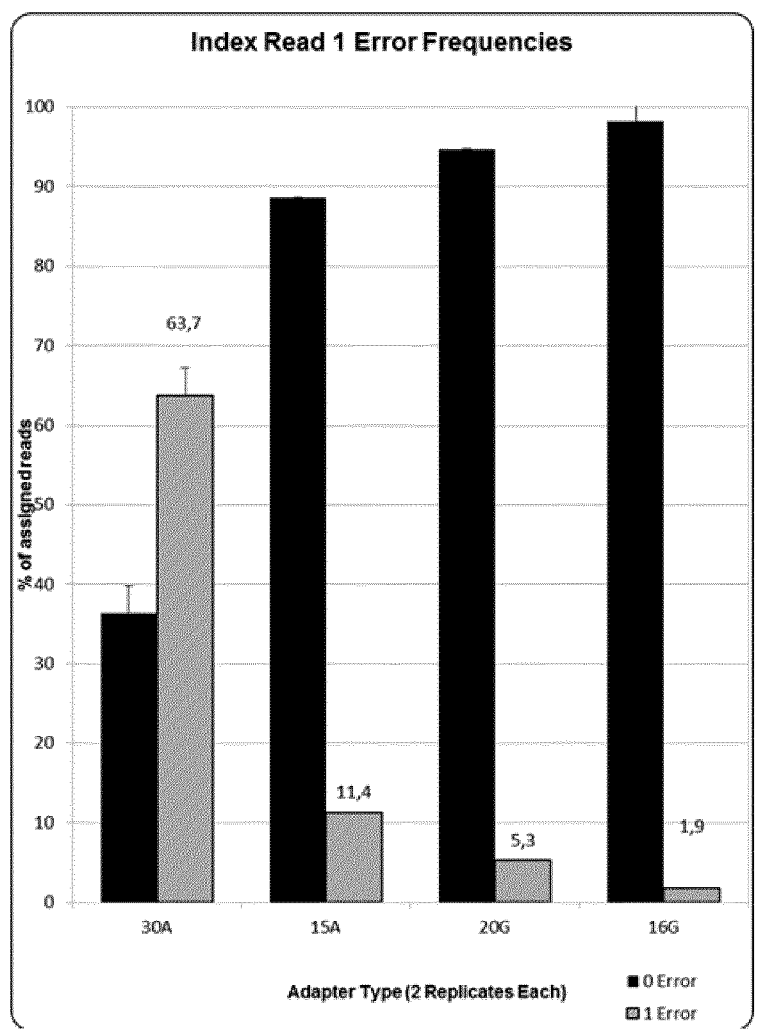

FIG. 7: Accuracy of the index read for multiplexed sample libraries in one sequencing lane depending on the sequence of the priming oligonucleotide. Shown are the respective ratios of index reads that were identified with zero errors and one error, depending on the sequence composition of the priming oligonucleotide used to generate the double stranded nucleic acid, more precisely on the portion complementary to the poly(A)tail created in the prior step of the method. Eight DNA fragment libraries were generated in parallel from identical (1 ng) amounts of the input source material (human genomic DNA), using four different priming oligonucleotides as shown and two replicates for each oligonucleotide. The eight resulting libraries were pre-amplified with primers as appropriate for multiplexed sequencing on current Illumina sequencer systems, each reverse primer including a different index sequence that is used to determine the library of origin for an identified read. The used index sequences correspond to Illumina index sequences 1-8 and each index sequence differs in at least 3 positions from all others. Equimolar amounts of each library were pooled and single-end sequenced on one lane with 70 cycles for read #1 and 6 cycles for the index read on an Illumina MiSeq system. For each of the eight libraries with different index sequences, the corresponding number of index read sequences containing no errors or one error were recorded. Depicted are the mean frequency values of index sequence reads with 0 or 1 error of the two libraries generated with each of the four different types of priming oligonucleotides, respectively, with error bars denoting the difference of the means to the values of the single libraries. Evidently, using the priming oligonucleotide "20G" allows a considerably increased accuracy of index read sequence compared to the "30A" priming oligonucleotide, while maintaining the same efficiency of DNA fragment library generation.

FIG. 8: The advantage of controllable vs. non-controllable polynucleotide tailing on DNA and RNA templates.

An example demonstrating beneficial effects of controllable poly(A)- and poly(dA)-tailing on the yield of cDNA generated from synthetic cel-miR-39 DNA (left) and cel-miR-39 RNA (right). Controllable poly(A)- and poly(dA)-tailing allows more efficient production of libraries using the same concentration of the RT primer, and/or when the concentration of ATP in the solution is suboptimal. If the ratio of ATP (or dATP) to RNA (or DNA) template is higher than optimal, than long (>300 nt) tails would result. Long polynucleotide tails decrease the effective concentration of poly(dT) primer what decrease the yield of the library and produce a smear of larger by-products on the gel since the excess of poly(dT) primer hybridizes to a site within the large poly(A) tail. A: Electropherogram of 3% agarose gel electrophoresis of DNA libraries obtained after poly(dA)-tailing of 1 ng cel-miR-39 DNA template and using 10 nM poly(dT) reverse primer (ILPdTPo) either in the presence (C) or absence (NC) of the blocking ddATP nucleotide (dATP/ddATP ratio 1/50). Note, significantly higher yield of the library after controllable poly(dA)-tailing is achieved with the same concentration of the reverse primer. B: electropherogram obtained after 3% agarose gel electrophoresis of DNA libraries obtained after poly(A)-tailing of 1 ng cel-miR-39 RNA template either in the presence (C) or absence (NC) of the blocking 3d-ATP nucleotide (ATP/3d-ATP ratio 1/30). Note, the ratio of ATP to RNA template (1 mM ATP to 1 ng 22 nt template) was suboptimal. Note, significantly higher yield of the library and absence of a smear of larger by-products is achieved with controllable tailing.

DETAILED DESCRIPTIONS OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise.

As used in this specification the term "nucleic acid" comprises polymeric or oligomeric macromolecules, or large biological molecules, essential for all known forms of life. Nucleic acids, which include DNA (deoxyribonucleic acid) and RNA (ribonucleic acid), are made from monomers known as nucleotides. Most naturally occurring DNA molecules consist of two complementary biopolymer strands coiled around each other to form a double helix. The DNA strand is also known as polynucleotides consisting of nucleotides. Each nucleotide is composed of a nitrogen-containing nucleobase as well as a monosaccharide sugar called deoxyribose or ribose and a phosphate group. Naturally occurring nucleobases comprise guanine (G), adenine (A), thymine (T), uracil (U) or cytosine (C). The nucleotides are joined to one another in a chain by covalent bonds between the sugar of one nucleotide and the phosphate of the next, resulting in an alternating sugar-phosphate backbone. If the sugar is desoxyribose, the polymer is DNA. If the sugar is ribose, the polymer is RNA. Typically, a polynucleotide is formed through phosphodiester bonds between the individual nucleotide monomers. In the context of the present invention the term "nucleic acid" includes but is not limited to ribonucleic acid (RNA), deoxyribonucleic acid (DNA), and mixtures thereof such as e.g. RNA-DNA hybrids (within one strand), as well as cDNA, genomic DNA, recombinant DNA, cRNA and mRNA. A nucleic acid may consist of an entire gene, or a portion thereof, the nucleic acid may also be a miRNA, siRNA, or a piRNA. MiRNAs are short ribonucleic acid (RNA) molecules, which are on average 22 nucleotides long but may be longer and which are found in all eukaryotic cells, i.e. in plants, animals, and some viruses, which functions in transcriptional and post-transcriptional regulation of gene expression. MiRNAs are post-transcriptional regulators that bind to complementary sequences on target messenger RNA transcripts (mRNAs), usually resulting in translational repression and gene silencing. Small interfering RNAs (siRNAs), sometimes known as short interfering RNA or silencing RNA, are short ribonucleic acid (RNA molecules), between 20-25 nucleotides in length. They are involved in the RNA interference (RNAi) pathway, where they interfere with the expression of specific genes. PiRNAs are also short RNAs which usually comprise 26-31 nucleotides and derive their name from so-called piwi proteins they are binding to. The nucleic acid can also be an artificial nucleic acid. Artificial nucleic acids include polyamide or peptide nucleic acid (PNA), morpholino and locked nucleic acid (LNA), as well as glycol nucleic acid (GNA) and threose nucleic acid (TNA). Each of these is distinguished from naturally-occurring DNA or RNA by changes to the backbone of the molecule.

The term "single stranded nucleic acid" (ss nucleic acid) as used in this specification refers to a nucleic acid which consists of only one polynucleotide strand. In contrast, a "double stranded nucleic acid" (ds nucleic acid) consists of two polynucleotide strands wherein the majority of nucleotides are paired according to base pairing rules (A with T and C with G in case of DNA, A with U and C with G in case of RNA and A with U, T with A or C with G in RNA/DNA hybrids), hydrogen bonds bind the nitrogenous bases of the two separate polynucleotide strands to make the double-stranded nucleic acid. Double strands are also tolerant of mismatches. A mismatch within a double strand occurs, if two nucleotides which are positioned at the same position in the opposing strands do not follow the base pairing rules. The number of mismatches tolerated within a given double strand is determined by the length of the double strand, the base composition, the temperature and buffer conditions, e.g. salt concentration. How these parameters influence double strand formation is well known in the art.

The term "wobble base" or "degenerate base" as used in the context of the present specification refers to a particular nucleotide position within a synthetic DNA or RNA oligonucleotide where more than one base possibility exist. A "wobble base" or "degenerate base" is a combination of dA, dT, dG, dC, dU, A, T, G, C or U in all possible molar ratios. The commonly used "wobble bases" or "degenerate bases" are a sequence of consecutive degenerate (wobble) DNA bases, preferably selected from N, V, H, D, B and J, wherein N is the product of the incorporation of a nucleotide from an equimolar mixture of dA, dT, dC and dG, i.e. it stands for any of dA, dT, dC and dG; B is the product of the incorporation of a nucleotide from an equimolar mixture of dT, dC and dG, i.e. it stands for any of dT, dC and dG; D is the product of the incorporation of a nucleotide from an equimolar mixture of dA, dT and dG, i.e. it stands for any of dA, dT, and dG; H is the product of the incorporation of a nucleotide from an equimolar mixture of dA, dT and dC, i.e. it stands for any of dA, dT, and dC; V is the product of the incorporation of a nucleotide from an equimolar mixture of dA, dC and dG, i.e. it stands for any of dA, dC and dG; J is the product of the incorporation of a nucleotide from a mixture of (0-100% dA) to (0-100% dG) to (0-100% dC) to (0-100% dT) to (0-100% dU) to (0-100% rA) to (0-100% rG) to (0-100% rC) to (0-100% rT) to (0-100% rU). Thus, an oligonucleotide which comprises a wobble base at a position will comprise one specific nucleotide from the respectively indicated mixture. On the other hand a mixture of oligonucleotides will comprise different oligonucleotides, which comprise at the respective position all nucleotides comprised in the respective mixture. The ratio of oligonucleotides comprising the different nucleotides is determined by the respective ratio of nucleotides incorporated at a given position. This is illustrated by the sequence ANG, which is an abbreviation for an equimolar mixture of four different oligonucleotides, namely, AAG, ACG, AGG, and ATG. Thus, if a primer or oligonucleotide is indicated to comprise a wobble base, this implies that a mixture of primers or oligonucleotides exists comprising the different nucleotides at that position.

The term "sample" is referring to a part or piece of a tissue, organ or individual, typically being smaller than such tissue, organ or individual, intended to represent the whole of the tissue, organ or individual. Upon analysis a sample provides information about the tissue status or the health or diseased status of an organ or individual. Examples of samples include but are not limited to fluid samples such as blood, serum, plasma, synovial fluid, lymphatic fluid, cerebrospinal fluid, meningeal fluid, glandular fluid, fine needle aspirate, spinal fluid and other body fluids (urine, saliva). Further examples of samples include cell cultures or tissue cultures. Further examples include as well liquid and solid biopsy samples or solid samples such as tissue extracts. Samples may comprise fossils, remnants from extinct organisms, plants, fruits, animals, microbes, bacteria, viruses, fungi or cells derived therefrom.

"Consecutive nucleotides" as used in this specification refers to a sequence comprised of nucleotides following one another uninterrupted.

The term "abasic nucleotide" as used in this specification refers to a compound which can link two nucleotides by forming phosphodiester bonds with the 3'-terminus of one of the nucleotides and the 5'-terminus of the other nucleotide, lacks a structure capable of base pairing, with any of the naturally occurring nucleotides, i.e. a pyrimidine or purine derivative, and which spans a distance between the 5'-OH and the 3'-OH of the flanking nucleotides that is at least 90% of the distance between the 5'-OH and the 3'-OH of a naturally occurring nucleotide. Preferably the distance is at least 91%, 92%, 93%, 94%, 95%, 96%, 97%, 98%, 99% or 100% of the distance between the 5'-OH and the 3'-OH of a naturally occurring nucleotide. The "abasic nucleotide" serves as a so-called "place holder" instead of a naturally occurring nucleotide. It is understood by the skilled person that the place holder should extend the nucleotide chain by a length that is similar to the extension through addition of a naturally occurring nucleotide. Thus, an abasic nucleotide allows the nucleotides preceding and following it to form Watson-Crick base pairs with three contiguous nucleotides, wherein the first and last base pair with the preceding and following nucleotide. The skilled person also appreciates that the reference to 3'-OH and 5'-OH is referring to the chemical groups that would be present at the 3'-position of the sugar backbone of the preceding nucleotide and the 5'-OH of the following nucleotide in the absence of the abasic nucleotide. If the abasic nucleotide is present it is preferred that it is linked to the preceding and following nucleotide by phosphodiester bonds. In DNA, abasic sites are generated by hydrolysis of the glycosidic linkage to the nucleotide base, leaving just the sugar-phosphate backbone at that position. In the cell, abasic site formation occurs after a spontaneous depurination/depyrmidination event, by UV ionizing radiation, or as a base excision repair intermediate. Because such sites are fragile, they are easily susceptible to single-stranded/double-stranded breakage, and if not repaired by the base excision repair mechanism, abasic lesions often lead to mutation by translesion synthesis during replication. The particular base incorporated opposite the lesion varies depending on organism and environmental conditions. A commonly used synthetic abasic nucleotide comprises abasic furan called dSpacer (1,2-dideoxyribose) which is a tetrahydrofuran derivative, in which a methylene group occupies the 1 position of 2-deoxyribose. dSpacer is commonly used to mimic an abasic site in an oligonucleotide. Other abasic nucleotides available comprise rSpacer, Spacer 18, Spacer 9, Spacer C3, Spacer C12.

The term "hybridizing" refers to the attachment of a single-stranded nucleic acid, preferable an oligonucleotide of a known sequence to a partially or fully complementary sequence of a single-stranded nucleic acid under specific temperature conditions, which are determined by to the composition of nucleobases and length of nucleotides. "Hybridization" can also be understood to refer to a process of detecting a certain nucleic acid sequences. A nucleic acid sequence encoding the complementary sequence of the sequence to be detected may be used as a hybridization probe according to standard hybridization techniques. "In situ hybridization" uses a labeled complementary nucleic acid molecule, e.g. a DNA or RNA strand (i.e. a probe) to localize a specific nucleic acid molecule, e.g. a DNA or RNA sequence, in a sample, e.g. in a portion or section of tissue (in situ). Hybridization conditions are known to those skilled in the art and can be found, for example, in Current Protocols in Molecular Biology, John Wiley & Sons, N.Y., 6.3.1-6.3.6, 1991. The term "moderate hybridization conditions" as used in the context of the present invention refers to hybridization in 2× sodium chloride/sodium citrate (SSC) at 30° C., followed by a wash in 1× SSC, 0.1% SDS at 50° C. "Highly stringent conditions" are hybridization in 6× sodium chloride/sodium citrate (SSC) at 45° C., followed by a wash in 0.2× SSC, 0.1% SDS at 65° C.

"Complementary" as used within this specification refers to a nucleotide sequence that baise-pairs by non-covalent bonds to all or a region of a target nucleic. In the canonical Watson-Crick base pairing adenine (A) forms a base pair with thymine, as does guanine with cytosine in DNA. In RNA, thymine is replaced by uracil. As such, A is complementary to T and G is complementary to C. In RNA, A is complementary to U and vice versa. Typically, complementary refers to a nucleotide sequence that is at least partially complementary. The term complementary may also encompass duplexes that are fully complementary such that every nucleotide in one strand is complementary to every nucleotide in the other strand in corresponding positions. In certain cases, a nucleotide may be partially complementary to a target in which not all nucleotides are complementary to every nucleotide in the target nucleic acid in all the corresponding positions. For example, a primer may be perfectly (i.e. 100%) complementary to the target nucleic acid, or the primer and the target nucleic acid may share some degree of complementarity which is less than perfect (i.e. 70%, 75%, 80%, 85%, 90%, 95%, 99%).

"Complementary DNA" (cDNA) as used within this specification is DNA synthesized from a RNA template in a reaction catalyzed by enzymes like, e.g. reverse transcriptase and DNA polymerase. cDNA is often used to clone eukaryotic genes in prokaryotes. cDNA is also produced naturally by retroviruses (such as HIV-1, HIV-2 or Simian Immunodeficiency Virus) and then integrated into the host's genome where it creates a provirus. The term cDNA is also used, typically in a bioinformatics context, to refer to an mRNA transcript's sequence, expressed as DNA bases (GCAT) rather than RNA bases (GCAU). "Complementary RNA" (cRNA) is understood as a RNA strand complementary to a given RNA template.

As used in this specification the term "template dependent DNA or RNA polymerase" refers to enzymes which comprise a catalytic activity capable of using a template nucleic acid strand and synthesize a second nucleic acid strand complementary to the template strand. These enzymes require a template which is used as a basis for the synthesized strand. A preferred example is a "reverse transcriptase" (RT) referring to an enzyme which is also named RNA-dependent DNA polymerase and is commonly used to generate complementary DNA from an RNA template, a process which is termed reverse transcription. The catalytic activities of the enzyme convert single-stranded genomic RNA in a first step into a RNA/DNA hybrid and in a second step into double stranded DNA. Sources of RT are retroviruses e.g. human immunodeficiency virus (HIV) which needs the RT for its replication. RT activity is also associated with the replication of chromosome ends (telomerases) and some mobile genetic elements (transposons). Usually, the RT comprises two sequential biochemical activities, a RNA-dependent DNA-Polymerase and a DNA polymerase, which work together to perform transcription. In addition to the transcription function, retroviral RTs have a domain belonging to the RNAse H family which is essential for replication. Preferably, RTs are used which possess RNAse H activity. RTs are used in the laboratory for molecular cloning, RNA sequencing, polymerase chain reaction and genome analysis. It has been shown that RT possess template switching activity meaning that it is able to switch from one template to another. RTs which are particularly suitable in the method, kits and uses of the present invention include but are not limited to HIV-1 reverse transcriptase from human immunodeficiency virus type 1 (PDB 1HMV), M-MLV reverse transcriptase from the moloney murine leukemia virus, AMV reverse transcriptase from the avian myeloblastosis virus and telomerases. RTs may comprise MMLV reverse transcriptase, which may be obtained from NEB, Superscript II or Superscript III reverse transcriptase, which may be obtained from Invitrogen, Multiscribe reverse transcriptase, which may be obtained from Applied Biosystems, SMART MMLV reverse transcriptase or SMARTScribe reverse transcriptase, which may be obtained from Clontech. A telomerase is another example of a reverse transcriptase found in many eukaryotes, including humans, which carries its own RNA template; this RNA is used as a template for DNA replication and which can be used in the context of the present invention.

The term "template independent DNA/RNA polymerases" refers to an enzyme catalyzing the addition of nucleotides to the 3' terminus of a DNA and/or RNA molecule. Unlike most DNA and/or RNA polymerases these polymerases do not require a template which is used as a basis to synthesize a corresponding strand. Preferred examples of such enzymes are DNA/RNA ligases, terminal transferases and poly (A, U or C)-polymerases. The preferred substrate of these enzymes is a 3'-overhang of a double stranded nucleic acid or a 3' end of a single stranded nucleic acid, but they can also add nucleotides to blunt or recessed 3' ends. Cobalt is a necessary cofactor for some of these enzymes, in particular for the terminal transferases, however the enzyme also catalyzes reaction upon Mg and Mn administration in vitro. Preferred examples of terminal transferases to be used in the context of the present invention are terminal deoxynucleotidyl transferase (TdT) also termed DNA nucleotidylexotransferase (DNTT) or poly-(N)-polymerases, wherein N means A, G or U. Poly-(N)-polymerase are preferred enzymes in the context of the present invention and comprise Poly-(A)-polymerases, which are a class of enzymes capable of the addition of a poly-A-tail to a single stranded nucleic acid. Naturally, the poly-(A)-tailing reaction takes place at the 3' end of primary transcript RNA. The poly-(A) tail consists of multiple adenosine monophosphates, a stretch that consists of only adenine bases. Naturally occurring poly-(A)-tailing produces mature mRNA for translation. The poly-A-polymerase can use cytosine as substrate to generate poly-(C)-tails. Furthermore, poly-(U)-polymerase and poly-(G)-polymerase can be used, which have the same functionality, but use uracil, adenine and guanine for the tailing reaction, respectively. For example, poly-(U)-polymerase can be used to catalyze the template independent addition of UMP from UTP or AMP from ATP to the 3' end of RNA and can thus, be used for poly-A- or for poly-U tailing. "DNA-ligase" are another preferred example of a template independent polymerase and refers to a specific type of enzyme, a ligase, which facilitates the joining of DNA strands together by catalyzing the formation of a phosphodiester bonds between the 3'-hydroxyl of one DNA end with the 5'-phosphoryl of another. RNA may also be ligated similarly. A co-factor is generally involved in the reaction, and this is usually ATP or $NAD^+$. DNA ligases can use mononucleotides di-, tri-, or n-nucleotides to generate a tail consisting of mono-di, tri, n-nucleotides, wherein "n" is preferably between 4 to 100 nucleotides.

In the context of the present invention it is preferred to ligate an oligonucleotide of known sequence to the 3'-hydroxy end of a single stranded DNA. Similarly, RNA-ligases are a specific type of enzyme that catalyzes the formation of one or more phosphodiester bonds between the 3'-hydroxyl of one RNA or DNA end with the 5'-phosphoryl of an RNA or DNA. A preferred RNA-ligase to be used in the context of the present invention is the T4 RNA ligase or the T7 RNA ligase which catalyzes the ligation of a 5' phosphoryl-terminated nucleic acid donor to a 3' hydroxyl-terminated nucleic acid acceptor through the formation of a 3'→5' phosphodiester bond, with hydrolysis of ATP to AMP and $PP_i$. RNA ligases can use dinucleoside pyrophosphates as substrates to generate a tail of mononucleotides and also can use di-, tri-, n-nucleotides to generate a tail consisting of di, tri, n-nucleotides.

The term "immobilization" as used in this specification refers to any method capable of the fixation of a nucleic acid on a surface. Surface immobilized DNA is required for the development of DNA chips and arrays, DNA sensors, or other sensing devices including microfluidics, in addition to gene delivery devices. The broad application range for all of these DNA-based systems is to a major extent found in the medical area, using the devices also in DNA sequencing and furthermore for food and environmental or forensic analyses. Depending on the different surfaces, various immobilization techniques (e.g. via physical adsorption, covalent, affinity binding, and matrix entrapment) were developed and optimized, which are described for carbonaceous materials (e.g. carbon nanotubes), silica and silicon surfaces, gold surfaces, the same as for more recently complex biocompatible surfaces (e.g. polymeric gels).

"Polymerase chain reaction" (PCR) is a biochemical technology in molecular biology used to amplify a single or a few copies of a piece of DNA across several orders of magnitude, generating thousands to millions of copies of a particular DNA sequence. Almost all PCR applications employ a heat-stable DNA polymerase, such as Taq polymerase (an enzyme originally isolated from the bacterium *Thermus aquaticus*). This DNA polymerase enzymatically assembles a new DNA strand from DNA building-blocks, the nucleotides, by using single-stranded DNA as a template and DNA oligonucleotides (also called DNA primers), which are required for initiation of DNA synthesis. The vast majority of PCR methods use thermal cycling, i.e., alternately heating and cooling the PCR sample through a defined series of temperature steps. A basic PCR set up requires several components and reagents. These components include a DNA template that contains the DNA region (target) to be amplified, two primers that are complementary to the 3' ends of each of the sense and anti-sense strand of the DNA target, a Taq polymerase or another DNA polymerase with a temperature optimum at around 70° C., deoxynucleoside triphosphates (dNTPs), the building-blocks from which the DNA polymerase synthesizes a new DNA strand, buffer solution, providing a suitable chemical environment for optimum activity and stability of the DNA polymerase, divalent cations, magnesium or manganese ions; generally $Mg^{2+}$ is used, but $Mn^{2+}$ can be utilized for PCR-mediated DNA mutagenesis, as higher $Mn^{2+}$ concentration increases the error rate during DNA synthesis or monovalent cation potassium ions. The above method may include nucleic acid labeling. A series of techniques are known to the skilled person allowing for labeling of DNA, RNA or oligonucleotides. These include for example Nick translational labeling, random primed DNA labeling, PCR labeling of DNA probes and oligonucleotide 3'/5' end labeling, transcriptional labeling of RNA probes, oligonucleotide 3'/5' end labeling and oligonucleotide tailing. PCR can be used in certain preferred embodiments of the method of the present invention, preferably subsequently to the synthesis of double stranded nucleic acid.

The term "sequence determination" as used within this specification refers to a variety of methods for determining the precise order of nucleotides within a DNA or RNA molecule, in other words the determination of the order of the four bases—adenine, guanine, cytosine, and thymine—in a strand of DNA, or uracil instead of thymine in case of RNA. DNA sequencing may be used to determine the sequence of individual genes, larger genetic regions (i.e. clusters of genes or operons), full chromosomes or entire genomes. Sequencing can provide the order of individual nucleotides in DNA or RNA isolated from cells of animals, plants, bacteria, archaea, or virtually any other source of genetic information.

The term "array" as used in this specification refers to nucleic acid microarray (also commonly referred to as DNA chip or biochip if DNA is immobilized) is a ordered arrangement of spots on a solid surface each comprising the same or different nucleic acids. Preferably, each spot only comprises identical nucleic acid molecules. The spots may take on any shape, preferably round or square. Such microarrays are used to measure the expression levels of large numbers of genes simultaneously or to genotype multiple regions of a genome. Each spot usually contains picomoles (10-12 pmoles) of DNA of a specific sequence, known as probes (or reporters or oligos). These can be a short section of a gene or other DNA element that are used to hybridize a cDNA or cRNA (also called anti-sense RNA) sample (called target) under high-stringency conditions. Probe-target hybridization is usually detected and quantified by detection of fluorophore-, silver-, or chemiluminescence-labeled targets to determine relative abundance of nucleic acid sequences in the target. The probes are synthesized and then attached via surface engineering to a solid surface by a covalent bond to a chemical matrix (via epoxy-silane, amino-silane, lysine, polyacrylamide or others). The solid surface can be glass or a silicon chip. DNA microarrays can be used to measure changes in expression levels, to detect single nucleotide polymorphisms (SNPs), or to genotype or targeted resequencing.

Embodiments

In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

In the work leading to the present invention, it was surprisingly shown that single stranded nucleic acids can be synthesized to double stranded nucleic acid with defined 3' and 5' ends in a fast way wherein the obtained double stranded nucleic acid is ready to be sequenced by current next generation sequencing technologies without any additional steps than in the method described in the invention.

Based on these results the present invention provides in a first aspect a method for the synthesis of double stranded nucleic acid with a defined 3' and 5' terminal nucleotide sequence from a sample comprising single stranded nucleic acid comprising the steps of:
a) providing a sample comprising single stranded or double stranded nucleic acid, optionally denaturing the double stranded nucleic acid;
b) adding at least 5 consecutive nucleotides to the 3-terminus of the single stranded or double stranded nucleic acid,
c) hybridizing a priming oligonucleotide complementary to the added nucleotide sequence and synthesizing a cDNA or cRNA with a template dependent DNA or RNA polymerase to generate a double stranded nucleic acid,
d) hybridizing a template switching oligonucleotide to said double stranded nucleic acid, and
e) extending the 3' end of the cDNA or cRNA strand to synthesize a double stranded nucleic acid, wherein one strand of the nucleic acid comprises the priming oligonucleotide, and a cDNA or a cRNA that is complementary to the single stranded nucleic acid and to the template switching oligonucleotide.

One of the purposes of the method of the present invention is the addition of a known nucleotide sequence also referred to in the context of this invention as defined sequence both to the 3' and 5'-prime end to a single or double stranded nucleic acid of unknown sequence. These added nucleotide sequences allow the specific annealing of oligonucleotides of identical and/or complementary sequence to the double stranded nucleic acid that is the product of the method of the invention and thus numerous subsequent manipulations of the double stranded nucleic acid, including capturing, amplification, extension etc. Preferably, each of the 3'-prime and 5'-prime "defined sequences" do not hybridize to each other and also are unlikely to hybridize to any of the nucleotides present in the sample under the conditions chosen for the subsequent manipulations of the double stranded nucleic acid that is the product of the method of the invention.

In a preferred embodiment of the first aspect present invention the sample is obtained from a liquid or solid biopsy or derived thereof, more preferably a blood sample, plasma sample, serum sample, body fluid sample, saliva sample, urine sample, semen sample, sample of the fluid from the pleural cavity, sample from the fluid from the peritoneal cavity, sample of the cerebrospinal fluid, smear from a epithelial surface, sputum sample, stool sample, ejaculate sample, tears sample, sweat sample, lymph fluid sample, bronchial lavage sample, pleural effusion sample, meningal fluid sample, glandular fluid sample, fine needle aspirates sample, micro dissected cells, nipple aspirates fluid sample, spinal fluid sample, conjunctival fluid sample, vaginal fluid sample, duodenal fluid sample, pancreatic juice sample, or bile sample. In a further preferred embodiment the sample is a forensic sample or an archaelogocial sample. More preferably the sample is obtained from fossils, remnants of extinct organisms, plants, fruits and animals, microbes, bacteria, viruses. In another more preferred embodiment the sample is obtained from a mammal, more preferably from a human subject. In a further preferred embodiment the sample is derived from human subject with a disorder. More preferably the sample comprises human venous blood, even more preferably human plasma. In another preferred embodiment, the sample comprising the single-stranded or double stranded nucleic acid, preferably human blood, a serum sample or blood plasma sample, is directly subjected to the method of the present invention without a prior step of isolating the nucleic acid from the sample taken from the patient. This is a preferred embodiment when the single-stranded or double stranded nucleic acid is DNA. More preferably, in case the sample is subjected directly to the method of the present invention, the sample is treated with an enzyme capable of cleaving peptide bonds in proteins, preferably a protease, in particular proteinase K, and incubated at an appropriate temperature for an appropriate time. It is preferred that the sample is provided by a method that does not bear a substantial health risk to the patient, e.g. by withdrawal of blood from a peripheral vein or artery. The sample employed in step a) may comprise single stranded and/or double stranded nucleic acids. If the sample comprises double stranded DNA it is preferred that a denaturation step is carried out prior to step a). Such a step may involve heat or chemical denaturation.

In preferred embodiment of the first aspect of the present invention, the single or double stranded nucleic acid is DNA or RNA. The DNA or RNA can be fragmented or bisulfite-converted RNA or DNA. In a more preferred embodiment the RNA or DNA comprised in the sample has an average length of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41,43, 44, 45, 46, 47, 48, 49, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, or 600 nucleotides. More preferably, said single stranded nucleic acid is RNA, even more preferably the single stranded nucleic acid is miRNA, small RNA or piRNA. In a further preferred embodiment the RNA does not naturally comprise a contiguous stretch of polyadenines, preferably of at least thirty polyadenines. In a further preferred embodiment the single-stranded nucleic acid is DNA.

Due to the sensitivity of the method of the present invention the amount of single or double stranded nucleic acid that needs to be provided in step a) can be very low and can still lead to double stranded nucleic acids. Thus, in a preferred embodiment the sample provided in step a) has a DNA and/or RNA concentration of less than 1 µg/µl, preferably less than 0.1 µg/µl, more preferably less than 0.01 µg/µl, more preferably less than 1 ng/µl, even more preferably less than 0.1 ng/µl, even more preferably less than 0.01 ng/µl, more preferably less than 1 pg/µl, even more preferably less than 0.1 pg/µl, more preferably less than 0.01 pg/µl, most preferably less than 1 fg/µl. The total DNA and/or RNA in a sample can also be very low and is preferably 5 pg. Preferably, 5 pg/µl may be used if the nucleic acid provided in step a) of the first aspect of the present invention is small RNA, 5 pg may be used if the nucleic acid provided in said step a) is DNA or ranges from 1 pg/µl to 5 ng/µl if the nucleic acid provided in said step a) is miRNA or siRNA.

Step b) of the method requires the addition of at least 5 consecutive nucleotides to the 3'-terminus of the single stranded nucleic acid. This stretch of consecutive nucleotides serves the purpose of allowing the subsequent hybridization of the priming oligonucleotide. It can serve as the 3'-prime defined sequence introduced in the method of the present invention. Accordingly the priming oligonucleotide and the consecutive nucleotides must comprise a sequence that is complementary to each other. This aim can be reached if consecutive nucleotides of known sequence are added, for example by adding a primer of a known sequence or by adding a consecutive stretch of known mono- or dinucleotides. It is not required that this stretch of nucleotides is added immediately 3' to the single stranded nucleic acid in as long as it is comprised in the contiguous stretch of nucleotides added. Another preferred embodiment of the first aspect of the invention comprises the addition of identical consecutive nucleotides to the 3' terminus of the single-stranded nucleic acid. Preferably the identical consecutive nucleotides selected from the group consisting of A, T, G, C, or U are added. Preferably, the number of identical consecutive nucleotides ranges from 10 to 500 consecutive nucleotides, i.e. 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500. More preferably, the number of consecutive identical nucleotides ranges from 10 to 100 consecutive identical nucleotides, more preferably from 15 to 50 consecutive identical nucleotides, more preferably 20 to 40 consecutive identical nucleotides or 30 to 100 consecutive identical nucleotides, i.e. 10, 15, 20, 25, 30, 40, 50, 60, 70, 80, 90, or 100. Thus, shorter stretches of consecutive nucleotides are preferred. A limited overhang at the 3' prime end leads to: (1) proportionally higher capacity of the priming oligonucleotide added in step c) of the method of the present invention to initiate the reverse transcription at the same concentrations; (2) allowing precise calculation of the optimal amounts of priming oligonucleotide added in step c) of the method of the present invention resulting in lower incidence of "empty" DNA by-products generated when the priming oligonucleotide interacts directly with TSO (3) lower incidence of the DNA products containing a polynucleotide stretch longer than 30 nucleotides due to the initiation of the reverse transcription at the remote sites from 3'-end of the template. The advantages (1), (2) and (3) results in a statistically significant increase of sensitivity of the method and allows DNA synthesis from lower concentrations of templates. Additionally when libraries are produced, shorter stretches of consecutive nucleotides provide the additional advantage of better, e.g. more complex library generation.

In another preferred embodiment the identical consecutive nucleotides comprise consecutive dinucleotides selected from the group consisting of AC, AG, AT, AU, CA, CG, CT, CU, GA, GC, GT, GU, TA, TG, TC or TU. In another preferred embodiment identical consecutive tri-, quadro- or pentanucleotides are added. To only add one type of nucleotides it is preferred that the nucleotides added in reaction step b) comprise, essentially only comprise or consist of only one nucleotide building block of the specific type to be added e.g. only A, G, C or T. However, it can be envisioned that the nucleotide building blocks used in step b) are not entirely homogenous but also comprise other nucleotide building blocks. In this case the different nucleotide building blocks will be added in a stochastic way that reflects their respective concentration in the reaction mixture. It is, therefore desirable in one embodiment of the method of the invention to keep the concentration of other nucleotides to a minimum to ascertain that a consecutive stretch of the intended nucleotide sequence is formed. However, the method of the present invention does not exclude embodiments using mixtures of buildings blocks in as long as the majority of added nucleotides comprise at least 10 consecutive nucleotides of known sequence.

There are different ways to limit the number of nucleotides added in this tailing reaction known to the skilled person. One preferred embodiment is the use of suboptimal concentrations of the nucleotide or dinucleotide that is incorporated. Suboptimal concentration is a molarity of a nucleotide or dinucleotide which is lower than a molarity of a nucleotide or dinucleotide recommended by the supplier/producer of the template independent DNA and RNA polymerases; and under which template independent DNA and RNA polymerases synthesizes polynucleotide tails are shorter than 1000 nt. In cases in which template independent DNA and RNA polymerases are used for the tailing reaction the skilled person can determine for the respective enzyme a concentration of nucleotides or dinucleotides in the respective reaction mixture that leads in a given time to the maximal number of added nucleotides or dinucleotides, i.e. the concentration of maximal enzyme processivity. This concentration is then considered the optimal concentration for this enzyme under the given reaction conditions (e.g. buffer, pH, temperature etc.). A "suboptimal concentration" of nucleotides/dinucleotides is a concentration that is at least 10 times lower than optimal nucleotide concentration, more preferably 100 times lower. It is preferred that the suboptimal concentration leads to a reduction of enzyme processivity, i.e. the number of nucleotide/dinucleotide added in a given time period, that is at least 10 times lower than the number of nucleotides/dinucleotides added at the optimal nucleotide concentration, more preferably 100 times lower. Preferably, the suboptimal concentration is in the range: 0.1 mM-0.01 mM of ATP for 10-20 min $E.coli$ Poly(A)Polymerase mediated reaction in Poly(A)Polymerase Reaction Buffer (50 mM Tris-HCl, 250 mM NaCl, 10 mM MgCl2 pH 7.9 at 25° C.); 0.001 mM-0.0001 mM of ATP in for 10-20 min $E.coli$ Poly(A)Polymerase mediated reaction in MMLV Reverse Transcriptase Reaction Buffer (50 mM Tris-HCl, 75 mM KCl, 3 mM MgCl2, 10 mM DTT pH 8.3 at 25° C.); 0.1 mM-0.01 mM of ATP in for 10-20 min Yeast Poly(A) Polymerase mediated reaction in MMLV Reverse Transcriptase Reaction Buffer (50 mM Tris-HCl, 75 mM KCl, 3 mM MgCl2, 10 mM DTT pH 8.3 at 25° C.); 0.1 mM-0.01 mM of dATP for 10-30 min Terminal Transferase mediated reaction in either Terminal Transferase Reaction Buffer (50 mM Potassium Acetate, 20 mM Tris-acetate, 10 mM Magnesium Acetate, pH 7.9 at 25° C.) or MMLV Reverse Transcriptase Reaction Buffer (50 mM Tris-HCl, 75 mM KCl, 3 mM MgCl2, 10 mM DTT, pH 8.3 at 25° C.). Optimal concentration is a molarity of a nucleotide or dinucleotide under which template independent DNA and RNA polymerases add polynucleotide tails of at least 30 nt but not more than 1000 nt to DNA and RNA templates. In cases in which template independent DNA and RNA polymerases are used for the tailing reaction the skilled person can determine for the respective enzyme a concentration of nucleotides or dinucleotides in the respective reaction mixture that leads in a given time to the optimal number of added nucleotides or dinucleotides. This concentration is then considered the optimal concentration for this enzyme under the given reaction conditions (e.g. buffer, pH, temperature etc.). A "suboptimal concentration" of nucleotides/dinucleotides is a concentration that is at least 10 times higher than optimal nucleotide concentration, more preferably 100 times higher. It is preferred that the optimal concentration leads to a reduction of enzyme processivity, i.e. the number of nucleotide/dinucleotide added in a given time period, that is at least 10 times lower than the number of nucleotides/dinucleotides added at the suboptimal nucleotide concentration, more preferably 100 times lower. Preferably, the optimal concentration is in the range: 0.1 mM-0.01 mM of ATP for 10-20 min $E.coli$ Poly(A)Polymerase mediated reaction in Poly(A) Polymerase Reaction Buffer (50 mM Tris-HCl, 250 mM NaCl, 10 mM MgCl2 pH 7.9 at 25° C.); 0.001 mM-0.0001 mM of ATP in for 10-20 min $E.coli$ Poly(A)Polymerase mediated reaction in MMLV Reverse Transcriptase Reaction Buffer (50 mM Tris-HCl, 75 mM KCl, 3 mM MgCl2, 10 mM DTT pH 8.3 at 25° C.); 0.1 mM-0.01 mM of ATP in for 10-20 min Yeast Poly(A)Polymerase mediated reaction in MMLV Reverse Transcriptase Reaction Buffer (50 mM Tris-HCl, 75 mM KCl, 3 mM MgCl2, 10 mM DTT pH 8.3 at 25° C.); 0.1 mM-0.01 mM of dATP for 10-30 min Terminal Transferase mediated reaction in either Terminal Transferase Reaction Buffer (50 mM Potassium Acetate, 20 mM Tris-acetate, 10 mM Magnesium Acetate, pH 7.9 at 25° C.) or MMLV Reverse Transcriptase Reaction Buffer (50 mM Tris-HCl, 75 mM KCl, 3 mM MgCl2, 10 mM DTT, pH 8.3 at 25° C.).

In another preferred embodiment this is achieved by the usage of blocking nucleotides or dinucleotides. Blocking nucleotides or dinucleotides are nucleotides or dinucleotides that prevent the addition of further nucleotides or dinucleotides once added. Typically oligonucleotides are extended by adding the next nucleotide to a hydroxy group positioned at the 3' position of the ribose or desoxyribose. If the 3' position of the ribose or desoxyribose is blocked no further nucleotides or dinucleotides can be added. Thus, the ribose or desoxyribose of a blocking nucleotide or of the 3'-terminal nucleotide of a dinucleotide does not allow the addition of a further nucleotide or dinucleotide. Prefered blocking nucleotides are 3d-ATP, 3-Me-ATP and ddATP. More preferably, ddATP or 3d-ATP is used. If a mixture of blocking nucleotides and non-blocking nucleotides is used the incorporation of the first blocking nucleotide into a growing oligonucleotide chain is a stochastic event and the likelihood of incorporation of the first blocking nucleotide after the incorporation of a given number of non-blocking nucleotides will depend on the ratio of blocking and non-blocking nucleotides present in the reaction mixture. Accordingly, the concentration of these blocking nucleotides or dinucleotides in the reaction mixture is lower than the concentration of non-blocking nucleotides or dinucleotides. The lower the relative amount of the blocking nucleotide or dinucleotide the longer the extension will proceed. Since the incorporation of the first blocking oligonucleotide is a stochastic event the length of the oligonucleotide added in the tailing reaction will vary within a given range. Preferably the concentration ratio of blocking to non-blocking nucleotides or dinucleotides is between 1 to 1 to 1 to 1000. Typically the concentrations used range from 0.1 to 0.001 mM, i.e. 0.09, 0.08, 0.07, 0.06, 0.05, 0.04, 0.03, 0.02, 0.01, 0.009, 0.008, 0.007, 0.006, 0.005, 0.004, 0.003, 0.002, 0.001 nM. Most preferably, 3d-ATP is used in a ratio of 1 to 30 relative to the concentration of ATP for Yeast Poly(A)Polymerase and in a ratio of 1 to 1,7 relative to the concentration of ATP for $E.coli$ Poly(A)Polymerase to obtain extension products with the average size of 30 nt. Most preferably, ddATP is used in a ratio of 1 to 30 relative to the concentration of dATP for Terminal Tranferase to obtain extension products with the average size of 30 ntIt is preferred that the conditions are chosen in such that on average not more than 50 nucleotides are added, preferably not more than 40, more preferably not more than 35, more preferably not more than 30, preferably not more than 25, most preferably not more than 20.

In those embodiments in which a short stretch of identical consecutive nucleotides is desired it is preferred that this is achieved by providing a mixture or ribo- or deoxyribonucleotides and a chain terminating nucleotide. If a length of 10 consecutive nucleotides is desired than a 1 to 10 mixture of a chain terminating nucleotide and of a ribo- or deoxyribonucleotides will lead on average to such length. The skilled person, thus knows how to generate consecutive stretches of nucleotides which on average have a length as set out above and preferably in the range of 30 to 100 nucleotides. Preferred chain terminating nucleotides are dideoxynucleotides.

In another preferred embodiment the consecutive identical nucleotides comprise a mixture of at least two ribonucleotides or deoxyribonucleotides.

The inclusion of some amounts of one additional nucleotide in the polynucleotide tailing reaction may have beneficial effect due to the fact that the polynucleotide tail will not be homogenous anymore while still having a similar efficiency of binding to priming oligonucleotide. At the same time, non-homogenous polynucleotide tails can be beneficial for pair-end sequencing using Illumina platform since the homonucleotide sequencing is very error prone. In a preferred example it is desirable to generate a mixture comprising non-homogenous nucleotides as the polynucleotide tail resulting from the addition of this mixture to the single or double stranded nucleic acid provided in step a) of the method of the present invention is beneficial for—after finishing step e) and subjecting the generated nucleic acid to sequence determination methods—pair-end sequencing using for example the Illumina platform since with homopolynucleotides undesirable interferences may occur.

Preferably, A, T, G or C is used in the context of single-stranded DNA and U or A are used in the context of single-stranded RNA.

In another embodiment of the first aspect of the present invention the addition of identical nucleotides in step b) is carried out by template independent DNA and RNA polymerases. Preferably, these proteins are terminal transferases, DNA or RNA ligases or poly N polymerases, wherein N is selected from A, G or U. An enzyme having terminal transferase activity is capable of adding ribo- or deoxyribodinucleotides, or multimers thereof to a 3'-OH end of a nucleic acid without the necessity of a complementary template strand. Preferred enzymes with this activity are selected from the group consisting of a terminal transferase, poly-(A)-polymerase, poly-(U)-polymerase, and poly-(G)-polymerase. RNA ligases or DNA ligases may add mononucleotides, dinucleotides, trinuclotides or oligonucleotides, preferably mononucleotides dinucleotides, trinuclotides are added. Preferred ligases are T4 RNA ligase or T7 RNA ligase. Said ligases may tail efficiently a RNA template which contains a 2'-O-methyl at the terminal 3'-end nucleotide. It is preferred that the RNA ligase uses a dinucleotide pyrophopsphate as substrate when adding mononucleotides.

Step c) comprises the hybridization of the priming oligonucleotide to the previously added nucleotide sequence. This step preferably involves an increase in temperature allowing the formation of base pairs between the priming oligonucleotide and the added consecutive nucleotides. In addition to a sequence capable of hybridizing to the added consecutive nucleotides the priming oligonucleotide comprises a further defined sequence, preferably 5'-prime, which can be used to specifically hybridize another oligonucleotide, e.g. an oligonucleotide for PCR amplification. This part preferably has a length between 5 and 100 nucleotides. Preferably, it further comprises a so-called hook structure at the 3' end. The hook is preferably a nucleotide that is different from the nucleotides that are capable of hybridizing to the added consecutive nucleotides and serves the purpose to position the priming oligonucleotide directly at or close to the 5'-prime end of the consecutive nucleotides added in step b). Preferably the priming oligonucleotide used in the method of the present invention comprises the following following sequence elements:

$$3'\text{-}W_m\text{-}X\text{-}Y_n\text{-}Z1_o\text{-}Q_t\text{-}Z2_s\text{-}5',$$

wherein

W at each instance is independently selected from dA, dG, dC, dT and dU;

X is selected from dA, dG, dC, dT, dU, rA, rG, rC, rT and rU;

Y is a polynucleotide of at least 10 nucleotides length, wherein 80% or more of the sequence is composed of an identical nucleotide or dinucleotide selected from dA, dG, dC, dT, dU, rA, rG, rC, rT, rU, AC, AG, AT, AU, CA, CG, CT, CU, GA, GC, GT, GU, TA, TC, TG, TU, AA, CC, GG, TT, UU, UA, UC, UG, and UT, wherein the other at 20% or less of the sequence is composed of nucleotides or dinucleotides that are different from the major nucleotide or dinucleotide and also selected from dA, dG, dC, dT, dU, rA, rG, rC, rT, rU, AC, AG, AT, AU, CA, CG, CT, CU, GA, GC, GT, GU, TA, TC, TG, TU, AA, CC, GG, TT, UU, UA, UC, UG, and/or UT, with the proviso that X is different from the nucleotide or dinucleotide that constitutes the majority of Y;

Q is a sequence of consecutive degenerate (wobble) DNA bases, preferably selected from N, V, H, D, B and J, wherein N is the product of the incorporation of a nucleotide from an equimolar mixture of dA, dT, dC and dG; B is the product of the incorporation of a nucleotide from an equimolar mixture of dT, dC and dG; D is the product of the incorporation of a nucleotide from an equimolar mixture of dA, dT and dG; H is the product of the incorporation of a nucleotide from an equimolar mixture of dA, dT and dC; V is the product of the incorporation of a nucleotide from an equimolar mixture of dA, dC and dG, J is the product of the incorporation of a nucleotide from amixture of (0-100% dA) to (0-100% dG) to (0-100% dC) to (0-100% dT) to (0-100% dU) to (0-100% rA) to (0-100% rG) to (0-100% rC) to (0-100% rT) to (0-100% rU);;

Z1 is a polynucleotide of at least 5 nucleotides length of defined sequence, wherein the sequence is different from $W_m\text{-}X\text{-}Y_n$, preferably the sequence is also different from $Q_t\text{-}Z2_s$;

Z2 is a polynucleotide of at least 5 nucleotides length of defined sequence, wherein the sequence is different from $Wm\text{-}X\text{-}Y_n\text{-}Z1_o\text{-}Q_t$;

m is an integer of 0 to 6, i.e. 0, 1, 2, 3, 4, 5 or 6;

n is an integer of 10 to 100, if Y is selected from dA, dG, dC, dT, dU, rA, rG, rC, rT, and rU, an integer of 5 to 50, if Y is selected from AC, AG, AT, AU, CA, CG, CT, CU, GA, GC, GT, GU, TA, TC, TG, TU, AA, CC, GG, TT, UU, UA, UC, UG and UT;

o is 0 or 1;

s is 0 or 1; and t is an integer of 0 to 6, i.e. 0, 1, 2, 3, 4, 5 or 6.

Y is the part of the priming oligonucleotide that is capable of hybridizing to the added consecutive nucleic acids. Thus, it is preferred that it has a sequence complementarity of at least 90% to the added nucleic acids. Accordingly, it preferably has a length that corresponds to the length of the added consecutive nucleotides, more preferably a length of between 10 to 100 nucleotides, i.e. 10, 15, 20, 25, 30, 35, 40, 45, 50, 55, 60, 65, 70, 75, 80, 85, 90, 95, or 100 nucleotides. It has been discovered by the present inventors that short Y improves sequence accuracy. However, to allow hybridization, preferably under stringent conditions, it is preferred that Y has a length of between 11 to 50, more preferably between 12 and 40, more preferably between 13 and 30 and most preferably between 14 and 20.

It has been discovered by the present inventors, that the presence of a low number of not identical nucleotides and/or dinucleotides improves sequencing accuracy. It is, thus preferred that the sequence of Y is composed of at least 80% of identical nucleotides and/or dinucleotides selected from dA, dG, dC, dT, dU, rA, rG, rC, rT, rU, AC, AG, AT, AU, CA, CG, CT, CU, GA, GC, GT, GU, TA, TC, TG, TU, AA, CC, GG, TT, UU, UA, UC, UG, and UT, wherein the other at 20% or less are composed of nucleotides or dinucleotides that are different from the major nucleotide and/or dinucleotide and also selected from dA, dG, dC, dT, dU, rA, rG, rC, rT, rU, AC, AG, AT, AU, CA, CG, CT, CU, GA, GC, GT, GU, TA, TC, TG, TU, AA, CC, GG, TT, UU, UA, UC, UG, and UT. In a preferred embodiment the major nucleotides are A and/or T. In another preferred embodiment the nucleotides are dinucleotides, preferably AA, TT, AT or TA. In another preferred embodiment the minor nucleotides are C and/or G. In another preferred embodiment the nucleotides are dinucleotides, preferably CC, GG, CG and/or GC In a preferred embodiment between 80% to 99% of the sequence of Y is composed of identical nucleotides and/or dinucleotides, more preferably between 85% to 95% (it is clear to the skilled person that in this case "n" has to be at least 20), more preferably 88% to 92% and most preferably about 90%. Thus, Y in an exemplary preferred embodiment may comprise 9 T nucleotides and one G or C nucleotide or 14 T and one G or C.

In cases in which Y comprises one or two different nucleotides it is preferred that this(ese) nucleotide(s) are located at or close to (i.e. within 1 to 4 bases) of the middle of Y.

In another preferred embodiment of the second aspect of the present invention it is preferred that Y is a consecutive stretch of nucleotides consisting only of T and n ranges from 10 to 60, i.e. 50, 45, 40, 35, 34, 33, 32, 31, 30, 29, 28, 27, 26, 25,24, 23, 22, 21, 20, 19, 18, 17, 16, 15, 14, 13, 12, 11, or 10, more preferably between 11 to 50, more preferably between 12 and 40, more preferably between 13 and 30 and most preferably between 14 and 20. More preferably, n is 30, 20, 16 or 15. It is most preferred that n is 20 or 16. In an alternative to this preferred embodiment Y comprises one or two different nucleotides, preferably G or C it is further preferred In an alternative preferred embodiment the sequence of Y is a consecutive stretch of nucleotides consisting only of T but for one or two G and/or C residues.

Z1 is the part of the priming oligonucleotide that is used subsequent to the synthesis of the double stranded nucleic acid molecule to allow sequence specific hybridization of another oligonucleotide. Thus, Z1 is preferably the defined sequence added to the 3'-prime end of the nucleic acid comprised in the sample. The length of Z1 is at least 5 nucleotides, more preferably in the range of 5 to 50 nucleotides, more preferably in the range of 10 to 30 nucleotides. The length is chosen in such that a primer can specifically hybridize to Z1 in subsequent PCR amplification reactions. In a preferred embodiment the nucleic acid sequence of Z1 is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

Preferably, Z1 is not identical to Z2.

Z2 is the part of the priming oligonucleotide that is used subsequent to the synthesis of the double stranded nucleic acid molecule to allow sequence specific hybridization of another oligonucleotide. Thus, Z2 is preferably the defined sequence added to the 3'-prime end of the nucleic acid comprised in the sample. The length of Z2 is at least 5 nucleotides, more preferably in the range of 5 to 50 nucleotides, more preferably in the range of 10 to 30 nucleotides. The length is chosen in such that a primer can specifically hybridize to Z1 in subsequent PCR amplification reactions. In a preferred embodiment the nucleic acid sequence of Z2 is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16 or the corresponding sequence.

Preferably, Z2 is not identical to Z1.

The inclusion of 1 to 6, more preferably 2 to 4, i.e. 1, 2, 3, 4, 5 or 6, consecutive wobble bases into the primer, i.e. between Z1 and Z2 will allow dissecting PCR duplicates in the library. Preferably, Q is a sequence of consecutive degenerate (wobble) DNA bases, preferably in each case independently selected from N, V, H, D, B and J, wherein N is the product of the incorporation of a nucleotide from an equimolar mixture of dA, dT, dC and dG; B is the product of the incorporation of a nucleotide from an equimolar mixture of dT, dC and dG; D is the product of the incorporation of a nucleotide from an equimolar mixture of dA, dT and dG; H is the product of the incorporation of a nucleotide from an equimolar mixture of dA, dT and dC; V is the product of the incorporation of a nucleotide from an equimolar mixture of dA, dC and dG, J is the product of the incorporation of a nucleotide from a mixture of (0-100% dA) to (0-100% dG) to (0-100% dC) to (0-100% dT) to (0-100% dU) to (0-100% rA) to (0-100% rG) to (0-100% rC) to (0-100% rT) to (0-100% rU);. The inclusion of consecutive wobble bases into the priming oligonucleotide is preferred because it helps to dissect PCR duplicates in the generated DNA library. It is most preferred that Q is positioned between Z1 and Z2 and is N. Preferably, Q is N and t is at least 2, more preferably 4.

In another preferred embodiment the sum of t and s is 0, e.g. Z2 and Q are absent.

Particularly preferred examples of the priming oligonucleotide are the nucleotides with nucleotide sequences according to SEQ ID NO: 17, SEQ ID NO: 18, SEQ ID NO: 19, and SEQ ID NO: 20.

Once the priming oligonucleotide is annealed its 3'-prime end is extended by a template dependent DNA or RNA polymerase, preferably a DNA or RNA polymerase that also has terminal transferase activity. Preferred examples of such enzymes are reverse transcriptases (RT), in particular MMLV RT. Once the end of the template is reached the template dependent DNA or RNA polymerase uses its terminal transferase activity to add additional nucleotides in a template independent manor. Thus, the product of step c) is a double stranded nucleic acid (DNA/DNA, RNA/RNA or DNA/RNA) with an overhang at the 3'-prime end of the newly synthesized strand. Preferably, this overhang has a length of at least 1 nucleotide, preferably of at least 3 nucleotides. Preferably, these nucleotides are identical.

They, are preferably selected from dA, dC, dG, dT, rA, rC, rG and rU, most preferably from dC. Thus, a particularly preferred overhang consists of a contiguous stretch of three cytosine nucleotides.

In step d) a template switching oligonucleotide (TSO) is hybridized to the product of step c), which allows the template dependent DNA or RNA polymerase, preferably an RT to add a defined sequence to the 5' prime end of the single stranded or double stranded nucleic acid comprised in the sample. This is achieved by further extending the 3' prime end of the nucleic acid strand synthesized in step c). The term "template switching oligonucleotide" is used to refer to an oligonucleotide template to which a polymerase activity switches from an initial template (e.g. the single-stranded nucleic acid provided by the sample of the present invention). In an embodiment of the present invention the template switching oligonucleotide is a DNA/RNA hybrid oligonucleotide, which is utilized by a template dependent DNA or RNA polymerase, preferably an RT, preferably MMLV RT to continue the reverse transcription after the enzyme, preferably the MMLV RT reaches the 5'-terminus of the template nucleic acid and adds through its terminal transferase activity nucleotides on the 3'-terminus of the synthesized cDNA or cRNA strand, i.e. template independent. The 3'-terminus of the TSO hybridizes to the nucleotides added by the terminal transferase activity of the template dependent DNA or RNA polymerase, effectively extending the 5'-terminus of the template DNA or RNA and thus enabling the template dependent DNA or RNA polymerase, preferably the RT, more preferably the MMLV RT to reversely transcribe also the remaining 5'-part of the TSO, which comprises a defined sequence to be added to the 5'-prime end of the template nucleic acid. As set out above regarding the priming oligonucleotide this defined sequence will not hybridize to the priming oligonucleotide sequence or its complementary sequence and will preferably also not hybridize to sequences present in the nucleic acid comprised in the sample. Preferably, it will not hybridize under the conditions typically employed in subsequent manipulations of the double stranded nucleic acid, which is the product of the method of the present invention, in particular PCR or sequence determination. The skilled person is well aware how to select suitable sequences that can serve as the defined sequence of the TSO. Furthermore, the TSO comprises at its 3'-prime end one or more nucleotides, preferably ribonucleotides that are complementary to the nucleotides added by the RT enzyme in step c). Preferably, the TSO comprised at its 3'-terminus 1 to 10, i.e. 1, 2, 3, 4, 5, 6, 7, 8, 9 or 10, preferably 3 consecutive nucleotides, preferably ribonucleotides. Preferably, if two or more nucleotides are added these nucleotides are identical.

In a preferred embodiment the TSO used in the method of the present invention is represented following sequence elements

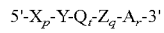

wherein

X is a chemical group selected from the group consisting of amino, biotin, glycerol, cholesterol, digoxigenin, fluoro residue or nucleotide derivatives including abasic nucleotides, dideoxy-ribonucleotides, 3'-deoxynucleotides, 2'-deoxyinosine, 2'-deoxyuridine;

Y is a known oligonucleotide sequence;

Q is a sequence of consecutive degenerate (wobble) DNA bases, preferably selected from N, V, H, D, B and J, wherein N is the product of the incorporation of a nucleotide from an equimolar mixture of dA, dT, dC and dG; B is the product of the incorporation of a nucleotide from an equimolar mixture of dT, dC and dG; D is the product of the incorporation of a nucleotide from an equimolar mixture of dA, dT and dG; H is the product of the incorporation of a nucleotide from an equimolar mixture of dA, dT and dC; V is the product of the incorporation of a nucleotide from an equimolar mixture of dA, dC and dG, J is the product of the incorporation of a nucleotide from a mixture of (0-100% dA) to (0-100% dG) to (0-100% dC) to (0-100% dT) to (0-100% dU) to (0-100% rA) to (0-100% rG) to (0-100% rC) to (0-100% rT) to (0-100% rU);

Z is a ribonucleotide selected from the group consisting of AMP, CMP, GMP, TMP and UMP, A is a chemical group selected from the group consisting of amino, biotin, glycerol, cholesterol, digoxigenin, phosphate, fluoro residue or nucleotide derivatives including abasic nucleotides, dideoxy-ribonucleotides, 3'-deoxynucleotides, 2'-deoxyinosine, 2'-deoxyuridine;

t is is an integer of 0 to 6, i.e. 0, 1, 2, 3, 4, 5 or 6;

p is an integer of 0 to 10, i.e. 0, 1, 2, 3, 4, 5, 6, 7, 8, 9 or 10;

q is an integer of at least 1; and r is an integer of 0 to 10, i.e. 0, 1, 2, 3, 4, 5, 6, 7, 8, 9 or 10.

It is understood by the skilled person that in cases in which a wobble base is included that claim actually refers to a mixture of TSOs which differ in sequence at the wobble base, where the relative abundance of one nucleotide over the other is determined by the respective molar ratio of the nucleotides in the nucleotide mixture used for synthesis of that nucleotide position in the TSO.

The addition of a bulky chemical group (e.g. biotin, several abasic nucleotides, fluorescent dye etc.) to the 5'-end of the TSO decreases the likelihood of secondary template switching events, and, thus, decrease the incidence of the DNA products containing two or more copies of the 5'-terminal sequence. Preferably X is biotin.

Y is a known sequence also referred to as defined sequence and thereby adds a nucleotide sequence at the 5'-terminus of the nucleic acid of step a) and subsequently into the double stranded nucleic acid produced in the method of the present invention that can be used in subsequent steps alone or in conjunction with the defined nucleic acid sequence added to the 3'-terminus of the single or double stranded nucleic acid in step b) to, e.g. amplify, detect or modify the double stranded nucleic acid resulting from step e) of the method of the invention. Thus, it is preferred that Y has a sufficient length to allow specific hybridization of an oligonucleotide, e.g. has a length between 15 to 50 nucleotides, more preferably between 20 and 40 nucleotides. Preferably, its sequence is distinct from any sequence found in the single or double stranded nucleic acid of step a) and also from any sequence added to the 3' in step b). In a preferred embodiment Y is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16 or the corresponding sequence.

The inclusion of 1 to 6, more preferably 2 to 4, i.e. 1, 2, 3, 4, 5 or 6, consecutive wobble bases into the reverse primer will help to dissect PCR duplicates in the library. Accordingly, in a preferred embodiment Q is N, V, H, D, B or J, where J is a mixture containing: (0-100% dA) to (0-100% dA) dG to (0-100% dA) dC to (0-100% dA) dT to (0-100% dA) dU to (0-100% dA) rA to (0-100% dA) rG to (0-100% dA) rC to (0-100% dA) rT to (0-100% dA) rU. The inclusion of consecutive wobble bases into the priming oligonucleotide is preferred because it helps to dissect PCR duplicates in the generated DNA library. It is most preferred that Q is positioned between Z1 and Z2 and is N. Preferably, Q is N and t is at least 2, more preferably 4.

The addition of the consecutive wobble bases will help to dissect PCR duplicates in the generated library. Preferably, Q is N and t is at least 2, more preferably 4.

The addition of a chemical "blocking" group (e.g. phosphate, biotin, methyl, fluorescent dye etc.) to the 3'-OH group of the 3'-terminal end of the TSO prevents the polynucleotide tailing of the TSO, which would occur if both polynucleotide tailing and reverse transcription are performed simultaneously. Also, addition of a chemical "blocking" group to the 3' prime end of the TSO would remove the requirements to heat inactivate template-independent DNA or RNA polymerase or ligase used in the tailing reaction before the RT reaction. Finally, an addition of a chemical "blocking" group to the TSO could reduce the bias towards templates carrying rG nucleotide at the 5'-end, a phenomenon observed when 3'-OH unblocked TSO are used on RNA templates. It is preferred that A is selected from the group consisting of amino, biotin, glycerol, cholesterol, digoxigenin, phosphate, fluoro residue or nucleotide derivatives including abasic nucleotides, dideoxy-ribonucleotides, 3'-deoxynucleotides, 2'-deoxyinosine, 2'-deoxyuridine. More preferably, A is an abasic nucleotide selected from the group consisting of abasic furan, rSpacer, Spacer 18, Spacer 9, Spacer C3 or Spacer C12. Even more preferably, A comprises more than one abasic site and is abasic furan, i.e. three consecutive abasic furans.

Step c) of the present invention comprises the hybridization of the priming oligonucleotide and the synthesis of a cDNA or cRNA with an appropriate enzyme to generate a double-stranded nucleic acid such as a reverse transcriptase. In a preferred embodiment the tailing reaction is carried out with a terminal deoxynucleotide transferase (step b)) and the hybridization reaction (step c)) with a reverse transcriptase. More preferably the reverse transcriptase used possesses simultaneously polymerase activity and terminal transferase activity and thus, the enzyme can be used to carry out step b) as well as step c) of the method of the present invention. Even more preferably, the enzyme reverse transcriptase is selected from the group consisting of the MMLV RT, which is, for example available from NEB, Superscript II RT or Superscript III RT, which is, for example, available from Invitrogen, Multiscribe RT, which is, for example, available from Applied Biosystems, SMART MMLV RT or SMART-Scribe RT, which is, for example, available from Clontech. In an even more preferred embodiment the M-MLV SuperScribe II RT or SmartScribe RT are used. It is preferred that polymerases are chosen that have both polymerase activity, i.e. that can synthesize a complementary nucleic acid based on a template nucleic acid, and terminal transferase activity, i.e. they are capable when reaching the 5' prime end of the single-stranded nucleic acid to add additional ribo- and/or deoxyribodinucleotides without a template. Preferably, they are capable of incorporating 1 or more, preferably 2 to 20, i.e. 2, 3, 4, 5, 6, 7, 8, 9, 10, 11, 12, 13, 14, 15, 16, 17, 18, 19, 20 additional ribo- and/or deoxyribodinucleotides to the 5' prime end of the single stranded nucleic acid, thereby enabling the hybridization between the template switching oligonucleotide and the 3' prime end of the nucleic acid strand. It is preferred that the reverse transcriptase incorporates predominantly a homonucleotide stretch, preferably a homotrinucleotide stretch which subsequently facilitates the hybridization of the reverse transcriptase from the template nucleic acid to the template swichting oligonucleotide. More preferably, three dCTPs or rCTPs are added.

In another embodiment of the present invention the synthesis of a double-stranded nucleic acid by the extension of the 3' prime end of cDNA or cRNA according to step e) of the method of the present invention requires an enzymatic activity. Hybridization of the TSO to the added homotrinucleotides of double stranded nucleic acid generated in step c) of the method of the present invention allows the elongation of the synthesized nucleic acid strand using the TSO as new template. Preferably, the reaction is carried out by a reverse transcriptase, more preferably by the MLLV reverse transcriptase. In a further preferred embodiment the reverse transcriptase used is able to switch to a template comprising a DNA/RNA and/or a DNA/DNA double-stranded nucleic acid.

Nucleic acids synthesized by the method of the present invention can be further analyzed in downstream applications, i.e. deep sequencing, genotyping, or cloning.

In one embodiment of the present invention the double-stranded nucleic acids are immobilized on a surface, preferably via physical adsorption, covalent binding, affinity binding or matrix entrapment. More preferably the nucleic acids of the present invention are immobilized on a microchip, a microarray surface, silica-based supports, next generation sequencing platform specific solid supports.

The method of the present invention may further include the step of using the synthesized double-stranded nucleic acid as a template for PCR amplification. According to one embodiment the method of the present invention further includes subjecting the synthesized double stranded nucleic acid or a single strand derived therefrom to amplification conditions. Such conditions may include the addition of a forward or reverse primer configured to amplify all or a desired portion of the synthesized double-stranded nucleic acid, dNTPS and a polymerase suitable for efficient amplification, preferably a thermostable polymerase. An initial step in carrying out the amplification may include the dentaturation of the double-stranded synthesized nucleic acid and making the synthesized nucleic acid available for primer binding. The synthesized double-stranded nucleic acid preferably comprises at least part of the priming oligonucleotide sequence, a complementary strand to the single-stranded nucleic acid provided, and at least a part of the TSO. These information about the two synthesized nucleic acid strands enable to provide oligonucleotides complementary to the respective sequences to generate larger amounts of the synthesized double-stranded nucleic acids. In a preferred embodiment the method of the present invention comprises the hybridization of at least one oligonucleotide capable of at least hybridizing to a part of the priming oligonucleotide of step c) or the template switching oligonucleotide of step d) to the double-stranded nucleic acid synthesized in step e). Preferably, one primer is complementary to the priming oligonucleotide and the other primer is complementary to the template switching oligonucleotide. Primer concentrations may be used in a concentration range from 200-300 nM, i.e. 210, 220, 230, 240, 250, 260, 270, 280, 290, 300 nM.

The amplification product of step f) of the method of the present invention can be further analyzed in downstream applications, i.e. deep sequencing, genotyping or cloning. In one embodiment of the present invention the amplification product is immobilized on a surface, preferably via physical adsorption, covalent binding, affinity binding or matrix entrapment.

By amplification of the synthesized double-stranded nucleic acid it is possible to produce large amounts of nucleic acid enabling a variety of downstream working technologies. As the synthesized nucleic acid possesses defined 3' prime and 5' prime ends determination of a sequence of interest within the provided single-stranded nucleic acid of the method of the present invention is enabled. Thus, in a preferred embodiment the method of the present invention further comprises the step of determining at least part of the sequence of the single-stranded nucleic acid. Preferably, the complete sequence of the single-stranded nucleic acid is determined.

The second aspect of the invention provides a priming oligonucleotide comprising the following sequence elements:

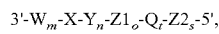

wherein

W at each instance is independently selected from dA, dG, dC, dT and dU;

X is selected from dA, dG, dC, dT, dU, rA, rG, rC, rT and rU;

Y is a polynucleotide of at least 10 nucleotides length, wherein 80% or more of the sequence is composed of an identical nucleotide or dinucleotide selected from dA, dG, dC, dT, dU, rA, rG, rC, rT, rU, AC, AG, AT, AU, CA, CG, CT, CU, GA, GC, GT, GU, TA, TC, TG, TU, AA, CC, GG, TT, UU, UA, UC, UG, and UT, wherein the other at 20% or less of the sequence is composed of nucleotides or dinucleotides that are different from the major nucleotide or dinucleotide and also selected from dA, dG, dC, dT, dU, rA, rG, rC, rT, rU, AC, AG, AT, AU, CA, CG, CT, CU, GA, GC, GT, GU, TA, TC, TG, TU, AA, CC, GG, TT, UU, UA, UC, UG, and/or UT, with the proviso that X different from the nucleotide or dinucleotide that constitutes the majority of Y;

Q is a sequence of consecutive degenerate (wobble) DNA bases, preferably selected from N, V, H, D, B and J, wherein N is the product of the incorporation of a nucleotide from an equimolar mixture of dA, dT, dC and dG, i.e. is dA, dT, dC or dG; B is the product of the incorporation of a nucleotide from an equimolar mixture of dT, dC and dG, i.e. is dT, dC and dG; D is the product of the incorporation of a nucleotide from an equimolar mixture of dA, dT and dG, i.e. is dA, dT, or dG; H is the product of the incorporation of a nucleotide from an equimolar mixture of dA, dT and dC, i.e. is dA, dT, or dC; V is the product of the incorporation of a nucleotide from an equimolar mixture of dA, dC and dG, i.e. is dA, dC or dG, J is the product of the incorporation of a nucleotide from a mixture of (0-100% dA) to (0-100% dG) to (0-100% dC) to (0-100% dT) to (0-100% dU) to (0-100% rA) to (0-100% rG) to (0-100% rC) to (0-100% rT) to (0-100% rU);

Z1 is a polynucleotide of at least 5 nucleotides length of defined sequence, wherein the sequence is different from $W_m$-X-$Y_n$, preferably the sequence is also different from $Q_r$-$Z2_s$;

Z2 is a polynucleotide of at least 5 nucleotides length of defined sequence, wherein the sequence is different from Wm-X-$Y_n$-$Z1_o$-$Q_r$;

m is an integer of 0 to 6, i.e. 0, 1, 2, 3, 4, 5 or 6;

n is an integer of 10 to 100, if Y is selected from dA, dG, dC, dT, dU, rA, rG, rC, rT, and rU, an integer of 5 to 50, if Y is selected from AC, AG, AT, AU, CA, CG, CT, CU, GA, GC, GT, GU, TA, TC, TG, TU, AA, CC, GG, TT, UU, UA, UC, UG and UT;

o is 0 or 1;

s is 0 or 1; and t is an integer of 0 to 6, i.e. 0, 1, 2, 3, 4, 5 or 6.

Y is the part of the priming oligonucleotide that is capable of hybridizing to the added consecutive nucleic acids. Thus, it is preferred that it has a sequence complementarity of at least 90% to the added nucleic acids. Accordingly, it preferably has a length that corresponds to the length of the added consecutive nucleotides, more preferably a length of between 10 to 100 nucleotides, i.e. 10, 15, 20, 25, 30, 35, 40, 45, 50, 55, 60, 65, 70, 75, 80, 85, 90, 95, or 100 nucleotides. It has been discovered by the present inventors that short Y improves sequence accuracy. However, to allow hybridization, preferably under stringent conditions, it is preferred that Y has a length of between 11 to 50, more preferably between 12 and 40, more preferably between 13 and 30 and most preferably between 14 and 20.

It has been discovered by the present inventors, that the presence of a low number of not identical nucleotides and/or dinucleotides improves sequencing accuracy. It is, thus preferred that the sequence of Y is composed of at least 80% of identical nucleotides and/or dinucleotides selected from dA, dG, dC, dT, dU, rA, rG, rC, rT, rU, AC, AG, AT, AU, CA, CG, CT, CU, GA, GC, GT, GU, TA, TC, TG, TU, AA, CC, GG, TT, UU, UA, UC, UG, and UT, wherein the other at 20% or less are composed of nucleotides or dinucleotides that are different from the major nucleotide and/or dinucleotide and also selected from dA, dG, dC, dT, dU, rA, rG, rC, rT, rU, AC, AG, AT, AU, CA, CG, CT, CU, GA, GC, GT, GU, TA, TC, TG, TU, AA, CC, GG, TT, UU, UA, UC, UG, and UT. In a preferred embodiment the major nucleotides are A and/or T. In another preferred embodiment the nucleotides are dinucleotides, preferably AA, TT, AT or TA. In another preferred embodiment the minor nucleotides are C and/or G. In another preferred embodiment the nucleotides are dinucleotides, preferably CC, GG, CG and/or GC In a preferred embodiment between 80% to 99% of the sequence of Y is composed of identical nucleotides and/or dinucleotides, more preferably between 85% to 95% (it is clear to the skilled person that in this case "n" has to be at least 20), more preferably 88% to 92% and most preferably about 90%. Thus, Y in an exemplary preferred embodiment may comprise 9 T nucleotides and one G or C nucleotide or 14 T and one G or C.

In cases in which Y comprises one or two different nucleotides it is preferred that this(ese) nucleotide(s) are located at or close to (i.e. within 1 to 4 bases) of the middle of Y.

In another preferred embodiment of the second aspect of the present invention it is preferred that Y is a consecutive stretch of nucleotides consisting only of T and n ranges from 10 to 60, i.e. 50, 45, 40, 35, 34, 33, 32, 31, 30, 29, 28, 27, 26, 25, 24, 23, 22, 21, 20, 19, 18, 17, 16, 15, 14, 13, 12, 11, or 10, more preferably between 11 to 50, more preferably between 12 and 40, more preferably between 13 and 30 and most preferably between 14 and 20. More preferably, n is 30, 20, 16 or 15. It is most preferred that n is 20 or 16. In an alternative to this preferred embodiment Y comprises one or two different nucleotides, preferably G or C it is further preferred In an alternative preferred embodiment the sequence of Y is a consecutive stretch of nucleotides consisting only of T but for one or two G and/or C residues.

Z1 is the part of the priming oligonucleotide that is used subsequent to the synthesis of the double stranded nucleic acid molecule to allow sequence specific hybridization of another oligonucleotide. Thus, Z1 is preferably the defined sequence added to the 3'-prime end of the nucleic acid comprised in the sample. The length of Z1 is at least 5 nucleotides, more preferably in the range of 5 to 50 nucleotides, more preferably in the range of 10 to 30 nucleotides. The length is chosen in such that a primer can specifically hybridize to Z1 in subsequent PCR amplification reactions. In a preferred embodiment the nucleic acid sequence of Z1 is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

Preferably, Z1 is not identical to Z2.

Z2 is the part of the priming oligonucleotide that is used subsequent to the synthesis of the double stranded nucleic acid molecule to allow sequence specific hybridization of another oligonucleotide. Thus, Z2 is preferably the defined sequence added to the 3'-prime end of the nucleic acid comprised in the sample. The length of Z2 is at least 5 nucleotides, more preferably in the range of 5 to 50 nucleotides, more preferably in the range of 10 to 30 nucleotides. The length is chosen in such that a primer can specifically hybridize to Z1 in subsequent PCR amplification reactions. In a preferred embodiment the nucleic acid sequence of Z2 is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16 or the corresponding sequence.

Preferably, Z2 is not identical to Z1.

The inclusion of 1 to 6, more preferably 2 to 4, i.e. 1, 2, 3, 4, 5 or 6, consecutive wobble bases into the primer, i.e. between Z1 and Z2 will allow dissecting PCR duplicates in the library. Preferably, Q is a sequence of consecutive degenerate (wobble) DNA bases, preferably in each case independently selected from N, V, H, D, B and J, wherein N is the product of the incorporation of a nucleotide from an equimolar mixture of dA, dT, dC and dG; B is the product of the incorporation of a nucleotide from an equimolar mixture of dT, dC and dG; D is the product of the incorporation of a nucleotide from an equimolar mixture of dA, dT and dG; H is the product of the incorporation of a nucleotide from an equimolar mixture of dA, dT and dC; V is the product of the incorporation of a nucleotide from an equimolar mixture of dA, dC and dG, J is the product of the incorporation of a nucleotide from a mixture of (0-100% dA) to (0-100% dG) to (0-100% dC) to (0-100% dT) to (0-100% dU) to (0-100% rA) to (0-100% rG) to (0-100% rC) to (0-100% rT) to (0-100% rU). The inclusion of consecutive wobble bases into the priming oligonucleotide is preferred because it helps to dissect PCR duplicates in the generated DNA library. It is most preferred that Q is positioned between Z1 and Z2 and is N. Preferably, Q is N and t is at least 2, more preferably 4.

In another preferred embodiment the sum of t and s is 0, e.g. Z2 and Q are absent.

Particularly preferred examples of the priming oligonucleotide are the nucleotides with nucleotide sequences according to SEQ ID NO: 17, SEQ ID NO: 18, SEQ ID NO: 19, and SEQ ID NO: 20.

In a third aspect the present invention provides a template switching oligonucleotide comprising the following sequence elements

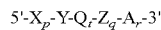

wherein

X is a chemical group selected from the group consisting of amino, biotin, glycerol, cholesterol, digoxigenin, fluoro residue or nucleotide derivatives including abasic nucleotides, dideoxy-ribonucleotides, 3'-deoxynucleotides, 2'-deoxyinosine, and 2'-deoxyuridine, preferably biotin Y is a known (defined) oligonucleotide sequence, Q is a sequence of consecutive degenerate (wobble) DNA bases, preferably selected from N, V, H, D, B and J, wherein N is the product of the incorporation of a nucleotide from an equimolar mixture of dA, dT, dC and dG; B is the product of the incorporation of a nucleotide from an equimolar mixture of dT, dC and dG; D is the product of the incorporation of a nucleotide from an equimolar mixture of dA, dT and dG; H is the product of the incorporation of a nucleotide from an equimolar mixture of dA, dT and dC; V is the product of the incorporation of a nucleotide from an equimolar mixture of dA, dC and dG, J is the product of the incorporation of a nucleotide from a mixture of (0-100% dA) to (0-100% dG) to (0-100% dC) to (0-100% dT) to (0-100% dU) to (0-100% rA) to (0-100% rG) to (0-100% rC) to (0-100% rT) to (0-100% rU);

Z is a ribonucleotide selected from the group consisting of AMP, CMP, GMP, TMP and UMP, preferably GMP, A is a chemical group selected from the group consisting of amino, biotin, glycerol, cholesterol, digoxigenin, phosphate, fluoro residue or nucleotide derivatives including abasic nucleotides, dideoxy-ribonucleotides, 3'-deoxynucleotides, 2'-deoxyinosine, and 2'-deoxyuridine, P is an integer of 0 to 10, i.e. 1, 2, 3, 4, 5, 6, 7, 8, 9 or 10, more preferably 1 or 2, most preferably 1, q is an integer of at least 1, preferably 1 to 10, i.e. 1, 2, 3, 4, 5, 6, 7, 8, 9, or 10, most preferably 3, r is an integer of 0 to 10, i.e. 0, 1, 2, 3, 4, 5, 6, 7, 8, 9, or 10, preferably 0 or 1, most preferably 0, and t is an integer of 0 to 6, i.e. 0, 1, 2, 3, 4, 5 or 6.

The addition of a bulky chemical group (e.g. biotin, several abasic sites, fluorescent dye etc.) to the 5'-end of the TSO decreases the likelihood of secondary template switching events, and, thus, decrease the incidence of the DNA products containing two or more copies of the 5'-termial sequence. Preferably X is biotin.

Y is a known sequence also referred to as defined sequence and thereby adds a nucleotide sequence at the 5'-terminus of the nucleic acid of step a) and subsequently into the double stranded nucleic acid produced in the method of the present invention that can be used in subsequent steps alone or in conjunction with the defined nucleic acid sequence added to the 3'-terminus of the single or double stranded nucleic acid in step b) to, e.g. amplify, detect or modify the double stranded nucleic acid resulting from step e) of the method of the invention. Thus, it is preferred that Y has a sufficient length to allow specific hybridization of an oligonucleotide, e.g. has a length between 15 to 50 nucleotides, more preferably between 20 and 40 nucleotides. Preferably, its sequence is distinct from any sequence found in the single or double stranded nucleic acid of step a) and also from any sequence added to the 3' in step b). In a preferred embodiment Y is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16 or the corresponding sequence.

In another preferred embodiment Q is a sequence of consecutive degenerate (wobble) DNA bases, preferably selected from N, V, H, D, B and J, wherein N is the product of the incorporation of a nucleotide from an equimolar mixture of dA, dT, dC and dG; B is the product of the incorporation of a nucleotide from an equimolar mixture of dT, dC and dG; D is the product of the incorporation of a nucleotide from an equimolar mixture of dA, dT and dG; H is the product of the incorporation of a nucleotide from an equimolar mixture of dA, dT and dC; V is the product of the incorporation of a nucleotide from an equimolar mixture of dA, dC and dG, J is the product of the incorporation of a nucleotide from amixture of (0-100% dA) to (0-100% dA) dG to (0-100% dA) dC to (0-100% dA) dT to (0-100% dA) dU to (0-100% dA) rA to (0-100% dA) rG to (0-100% dA) rC to (0-100% dA) rT to (0-100% dA) rU A serves the function as described above in the context of the first aspect of the present invention. Preferably, A is selected from the group consisting of amino, biotin, glycerol, cholesterol, digoxigenin, phosphate, fluoro residue or nucleotide derivatives including abasic nucleotides, dideoxy-ribonucleotides, 3'-deoxynucleotides, 2'-deoxyinosine, 2'-deoxyuridine. More preferably, A is an abasic nucleotide selected from the group consisting of abasic furan, rSpacer, Spacer 18, Spacer 9, Spacer C3 or Spacer C12. Even more preferably, A comprises more than one abasic site, i.e. three consecutive abasic furans.

In a fourth aspect the present invention provides a nucleic acid comprising the priming oligonucleotide of the second aspect of the invention. Preferably, the nucleic acid contains the sequence of the used priming oligonucleotide.

In a fifth aspect of the present invention provides a kit providing the performance of the method of the first aspect of the present invention. The kit may comprise reagents necessary to carry out every method step a) to f) of the present invention. The kit may include e.g. one or more of any of the reaction mixture components describe with respect to the subject of method steps a) to f). For example, the kit may comprise a polymerase (e.g. a polymerase capable of template switching, a thermostable polymerase or combinations thereof), a priming oligonucleotide, a template switch oligonucleotide, dNTPS, salts, suitable cofactors for enzymes, nuclease inhibitors, e.g. an RNAse inhibitor or a DNAse inhibitor, one or more additives for facilitating amplification or replication of GC rich sequences (e.g. Betaine, dimethylsulfoxid, ethylene glycol or 1,2 propandiol or combinations thereof, one or more destabilizing agents e.g. dithioreitol, an enzyme capable of generating double-strandend nucleic acid having 3' overhang (e.g. restriction endonucleases, a terminal transferase or a combination thereof) and a blocking nucleotide preferably 3d-NTP, 3-Me-NTP and ddNTP or any other desired kit component such as tubes, beads, microfluidic chips and the like. In a preferred embodiment of the kit of the present invention the subject kits include a reagent capable of adding nucleotides to the 3-terminus of the single stranded nucleic acid, preferably an enzyme, more preferably a poly-A polymerase or a terminal transferase. It is preferred that the kit also comprises a priming oligonucleotide and a template switch oligonucleotide and optionally an enzyme capable of cleaving peptide bonds in proteins, more preferably this enzyme is an endo- or exopeptidase, most preferably proteinase K. In another preferred embodiment of this aspect the kit may provide reagents necessary to carry out sequence determination methods. More preferably the reagents supplied by the kit provide tools for next generation sequencing, e.g. target enrichment with capture probes.

In a sixth aspect the present invention provides an array comprising at least one nucleic acid of the fourth aspect of the present invention. Preferably, the array allows sequence determination of said nucleic acid sequence. More preferably the array can be used to measure changes in expression levels, to detect single nucleotide polymorphisms (SNPs), or to genotype or targeted resequencing or provide a tool for deep sequencing.

Massive parallel sequencing (MPS) technologies have path the way into new areas in several fields of research such as individualized medicine. It is desirable to provide both the sequence and frequency of nucleic acid molecules that are present at any particular time in a specific cell type, tissue or organ. For example, counting the number of mRNAs that are encoded by individual genes (the so-called transcriptome) provides an indicator of protein-coding potential, a major contributor to phenotype. In a seventh aspect the present invention provides a use of the double-stranded nucleic acid synthesized by the method of the present invention or a single-stranded nucleic acid derived therefrom. In a preferred embodiment the nucleic acids synthesized by the method of the present invention can be used for sequencing or expression analysis, cloning, labeling, for identifying genes or certain nucleotide sequences. Preferably the use comprises application in personalized medicine, therapy monitoring; prediction, prognosis, early detection of human or animal disease or forensic science, analysis of nucleic acid sequences of viruses, bacteria, fungi, animals or plants or cells derived therefrom, preferably for characterization of plants, fruit breeding checks, detection of disease of plants, seeds or fruits.

EXAMPLES

Example 1

RNA and DNA Samples

Synthetic cel-miR-39 (Sigma-Aldrich), a 22 nt microRNA from *C.elegans* was used as an input for small RNA sequencing control. Synthetic 22 nt DNA (Sigma-Aldrich) with the sequence equal to the cel-miR-39 was used as an input for DNA sequencing control. Circulating DNA was isolated from the plasma fraction of blood samples from two voluntary healthy donors (DI, female and DII, male). The circulating RNA was isolated from the blood plasma of two voluntary female healthy donors (RI and RII). This samples collection was approved by the Ethical Committee of the Medical Faculty in Heidelberg. Circulating DNA and RNA isolated from human blood plasma, bisulfite-converted DNA from U2OS cells and $Mg^{2+}$ fractionated polyA enriched total RNA from U2OS cells were used as inputs for cDNA library preparation and subsequent Illumina MiSeq sequencing.

Example 2

Oligonucleotides for cDNA Synthesis

The sequences of all primers used in this work are provided in the FIGS. 2-5. Several template switch oligonucleotides (TSO) of different structures were tested during the development of the method.

Example 3

First-Strand cDNA Synthesis and Template Switching

Synthetic small RNA or DNA was diluted in water to achieve concentrations of 1 ng/μl and 5 pg/μl and was used as starting material to synthesize first-strand cDNA. The optimized protocol to generate the ready-to-sequence DNA library was as follows. The RNA was polyadenylated using E.coli poly(A) polymerase (New England Biolabs) in 1× PAP buffer containing 10 units Recombinant RNAse inhibitor (Clontech) and 0.1 mM ATP for 10 min at 37° C. and terminated by heating at 65° C. for 20 min. The DNA was poly(dA) tailed using terminal deoxynucleotide transferase (New England Biolabs) in 1× TdT buffer and 0.1 mM dATP for 30 min at 37° C. and heat inactivated for 10 min at 70° C. Before poly(dA) tailing, circulating DNA and bisulfite-converted DNA samples were denatured by heating at 95° C. for 5 min and fast cooling on ice. In some experiments RNA and DNA templates were pre-treated with T4 Polynucleotide Kinase (New England Biolabs) for 10 min in 1×PAP/TdT buffer before poly(A/dA) tailing. For the reverse transcription, 1 μl of poly(A) tailed RNA or poly(dA) tailed DNA was mixed with 2.5 μl of 1× First-Strand RT buffer containing 20% DMSO and 1 μl of the one-base anchored Illumina poly(dT) primer (final concentration 0.1 μM for 1 ng and 0.001 μM for 5 pg of RNA or DNA). The entire solution was incubated at 72° C. for 2 min and then cooled to 42° C. for 1 min. In the following step a master mix containing 2 μl 5× First-Strand RT buffer (Clontech), 1 μl dNTP (10 mM each), 1 μl SmartScribe RT polymerase (Clontech), 0.25 μl DTT (100 mM) and 0.25 μl of Recombinant RNAse Inhibitor (Clontech) was added to the DNA(RNA)/primer solution and incubated for 15 min at 42° C. Next, 1 μl of 10 μM 5'-biotin blocked template switch oligonucleotide (TSO) was added to the RT reaction and incubated for another 15 min at 42° C. The RT reaction was terminated by heating at 70° C. for 10 min. Either 1 μl or 10 μl of RT reaction was used for cDNA amplification in a total volume of 100 μl. The amplification of cDNA was performed in 2×Taq polymerase master mix (Qiagen) using cDNA amplification primers (FIG. 2A) at a final concentration of 250 nM. The amplified cDNAs were column purified using Qiaquick PCR Purification kit (Qiagen) and sequenced using Sanger automated sequencing by the GATC GmbH (Konstanz, Germany). For next generation sequencing, the DNA fragments were additionally purified from 4% agarose gel using PureLink Gel Extraction kit (Life Technologies) and analysed with Agilent Bioanalyser High Sensitivity DNA chips.

Example 4

Deep Sequencing

Illumina MiSeq platform was used to sequence DNA libraries prepared by the method described above. A custom sequencing primer consisting of Illumina standard sequencing primer and the 3'-terminal GGG trinucleotide was used for Illumina MiSeq sequencing to resolve the problem with required complexity of the first several bases needed for successful clusters identification. A custom poly(T) sequencing primer can be used for sequencing in the reverse direction, enabling the generation of paired end sequencing data. DNA libraries were diluted to a concentration of 5 nM, denatured with 0.2 N NaOH for 5 min and further diluted to 11 pM shortly before loading into the MiSeq cassette. The MiSeq run was performed using MiSeq Reagent Kit (50-cycles) for 77 cycles.

The invention claimed is:

1. A method for the synthesis of double stranded nucleic acid with a defined 3' and 5' terminal nucleotide sequence from a sample comprising single stranded nucleic acid comprising the steps of:
   a) providing a sample comprising single stranded or double stranded nucleic acid,
   b) performing a polynucleotide tailing reaction by adding at least 5 consecutive nucleotides to the 3'-terminus of the single stranded or double stranded nucleic acid,
   c) hybridizing a priming oligonucleotide complementary to the added nucleotide sequence and synthesizing a cDNA or a cRNA with a template dependent DNA or RNA polymerase to generate a double stranded nucleic acid,
   d) hybridizing a template switching oligonucleotide to said double stranded nucleic acid, and
   e) extending the 3' end of the cDNA or the cRNA strand to synthesize a double stranded nucleic acid, wherein one strand of the nucleic acid comprises the priming oligonucleotide, and a cDNA or a cRNA that is complementary to the single stranded nucleic acid and to the template switching oligonucleotide;
   wherein said priming oligonucleotide comprises the following nucleotide sequence elements:

$3'-W_m-X-Y-Z1_o-Q_t-Z2_s-5'$, wherein:
   W at each instance is independently selected from dA, dG, dC, dT and dU;
   X is selected from dA, dG, dC, dT, dU, rA, rG, rC, rT and rU;
   Y is a polynucleotide of between 15 and 100 nucleotides length, wherein between 80% and 99% of the sequence is composed of dT or rT, wherein the other 1% to 20% of the sequence is composed of nucleotides or dinucleotides that are different from dT or rT, and are selected from dA, dG, dC, dT, dU, rA, rG, rC, rT, rU, AC, AG, AT, AU, CA, CG, CT, CU, GA, GC, GT, GU, TA, TC, TG, TU, AA, CC, GG, UU, UA, UC, UG, and UT, with the proviso that at least one of the nucleotides in the sequence is different from dT or rT, and with the proviso that X is different from the nucleotide or dinucleotide that constitutes the majority of Y;
   Q is a sequence of consecutive degenerate (wobble) DNA bases;
   Z1 is a polynucleotide of at least 5 nucleotides length of defined sequence, wherein the sequence is different from $W_m-X-Y$;
   Z2 is a polynucleotide of at least 5 nucleotides length of defined sequence, wherein the sequence is different from $Wm-X-Y-Z1_o-Q_t$;
   m is an integer of 0 to 6, i.e. 0, 1, 2, 3, 4, 5 or 6;
   o is 0 or 1;
   s is 0 or 1; and
   t is an integer of 0 to 6, i.e. 0, 1, 2, 3, 4, 5 or 6.

2. The method according to claim 1, wherein the sample is a liquid or solid biopsy or derived thereof.

3. The method according to claim 1, wherein the sample is obtained from fossils, remnants of extinct organisms, plants, fruits and animals, microbes, bacteria, or viruses.

4. The method according to claim 1, wherein the single stranded nucleic acid is DNA.

5. The method according to claim 1, wherein the consecutive nucleotides are identical, or consist of identical dinucleotides, trinucleotides, quadranucleotides, pentanucleotides or polynucleotides.

6. The method according to claim 5, wherein the consecutive nucleotides are selected from the group consisting of identical ribonucleotides, deoxy-ribonucleotides or dideoxy-ribonucleotides of A, T, G, C, or U, or are selected from the group consisting of two or more ribo-dinucleotides or two or more deoxy-ribodinucleotides.

7. The method according to claim 1, wherein the polynucleotide tailing reaction of step b) is performed with a mixture of two or more ribonucleotides or deoxyribonucleotides.

8. The method according to claim 6, wherein the identical ribonucleotides, deoxy-ribonucleotides or dideoxy-ribonucleotides are added by an enzyme selected from the group consisting of poly(A)-polymerase, poly(U)-polymerase, poly(G)-polymerase, terminal transferase, a DNA ligase, and an RNA ligase, or wherein the two or more are added by an RNA ligase.

9. The method according to claim 1, wherein Z1 and/or Z2 is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

10. The method according to claim 1, wherein said template switching oligonucleotide is represented by the formula $$5'\text{-}X_p\text{-}Y\text{-}Q_t\text{-}Z_q\text{-}A_r\text{-}3'$$

wherein
X is a chemical group selected from the group consisting of amino, biotin, glycerol, cholesterol, digoxigenin, fluoro residue or nucleotide derivatives including abasic nucleotides, dideoxy-ribonucleotides, 3'-deoxynucleotides, 2'-deoxyinosine, 2'-deoxyuridine;
Y is a known oligonucleotide sequence;
Q is a sequence of consecutive degenerate (wobble) DNA bases;
Z is a ribonucleotide selected from the group consisting of AMP, CMP, GMP, TMP and UMP,
A is a chemical group selected from the group consisting of amino, biotin, glycerol, cholesterol, digoxigenin, phosphate, fluoro residue or nucleotide derivatives including abasic nucleotides, dideoxy-ribonucleotides, 3'-deoxynucleotides, 2'-deoxyinosine, 2'-deoxyuridine;
t is an integer of 0 to 6, i.e. 0, 1, 2, 3, 4, 5 or 6;
p is an integer of 0 to 10, i.e. 0, 1, 2, 3, 4, 5, 6, 7, 8, 9 or 10;
q is an integer of at least 1; and
r is an integer of 0 to 10, i.e. 0, 1, 2, 3, 4, 5, 6, 7, 8, 9 or 10.

11. The method according to claim 10, wherein Y of the template switching oligonucleotide is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

12. The method according to claim 1, wherein said reverse transcriptase possesses DNA-polymerase activity and terminal transferase activity.

13. The method according to claim 1, wherein said reverse transcriptase is able to switch to a template comprising a DNA/RNA and/or a DNA/DNA double stranded nucleic acid.

14. The method according to claim 1, further comprising the step of immobilizing the synthesized double stranded nucleic acid on a surface.

15. The method according to claim 1, further comprising the step f) of annealing to the double stranded nucleic acid synthesized in step e) at least one primer identical, complementary or capable of hybridizing to at least part of the priming oligonucleotide or the template switching oligonucleotide and carrying out a PCR amplification.

16. The method according to claim 15, further comprising the step of immobilizing the product of the PCR amplification.

17. The method according to claim 15, further comprising the step of determining at least part of the sequence of the single stranded nucleic acid.

18. A method for the synthesis of double stranded nucleic acid with a defined 3' and 5' terminal nucleotide sequence from a sample comprising single stranded nucleic acid comprising the steps of:
a) providing a sample comprising single stranded or double stranded nucleic acid,
b) performing a polynucleotide tailing reaction by adding at least 5 consecutive nucleotides to the 3'-terminus of the single stranded or double stranded nucleic acid,
c) hybridizing a priming oligonucleotide complementary to the added nucleotide sequence and synthesizing a cDNA or a cRNA with a template dependent DNA or RNA polymerase to generate a double stranded nucleic acid,
d) hybridizing a template switching oligonucleotide to said double stranded nucleic acid, and
e) extending the 3' end of the cDNA or the cRNA strand to synthesize a double stranded nucleic acid, wherein one strand of the nucleic acid comprises the priming oligonucleotide, and a cDNA or a cRNA that is complementary to the single stranded nucleic acid and to the template switching oligonucleotide;
wherein said template switching oligonucleotide is represented by the formula $$5'\text{-}X_p\text{-}Y\text{-}Q_t\text{-}Z_q\text{-}A_r\text{-}3'$$

wherein
X is a chemical group selected from the group consisting of amino, biotin, glycerol, cholesterol, digoxigenin, fluoro residue or nucleotide derivatives including abasic nucleotides, dideoxy-ribonucleotides, 3'-deoxynucleotides, 2'-deoxyinosine, 2'-deoxyuridine;
Y is a known oligonucleotide sequence;
Q is a sequence of consecutive degenerate (wobble) DNA bases;
Z is a ribonucleotide selected from the group consisting of AMP, CMP, GMP, TMP and UMP,
A is a chemical group selected from the group consisting of amino, biotin, glycerol, cholesterol, digoxigenin, phosphate, fluoro residue or nucleotide derivatives including abasic nucleotides, dideoxy-ribonucleotides, 3'-deoxynucleotides, 2'-deoxyinosine, 2'-deoxyuridine;
t is an integer of 0 to 6;
p is an integer of 0 to 10;
q is an integer of at least 1; and
r is an integer of 0 to 10;
wherein Y is selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

19. The method according to claim 18, wherein said template switching oligonucleotide comprises SEQ ID NO: 25.

20. The method according to claim 1, wherein the priming oligonucleotide comprises the sequence selected from the group consisting of SEQ ID NO: 17, SEQ ID NO: 18, SEQ ID NO: 19, and SEQ ID NO: 20.

* * * * *